United States Patent
Nadas et al.

(10) Patent No.: US 8,165,895 B2
(45) Date of Patent: Apr. 24, 2012

(54) SYSTEM AND METHOD FOR SELECTING COMPLIANCE RELATED SERVICES

(75) Inventors: Gyula J. Nadas, Wauconda, IL (US); Hee K. Oh, Wilmette, IL (US); Laura J. Tebbe, Lindenhurst, IL (US); Steve S. Dorfman, Chicago, IL (US); Amanda White, Schaumburg, IL (US)

(73) Assignee: Walgreen Co., Deerfield, IL (US)

( * ) Notice: Subject to any disclaimer, the term of this patent is extended or adjusted under 35 U.S.C. 154(b) by 386 days.

(21) Appl. No.: 11/959,242

(22) Filed: Dec. 18, 2007

(65) Prior Publication Data

US 2009/0043608 A1 Feb. 12, 2009

Related U.S. Application Data

(60) Provisional application No. 60/963,871, filed on Aug. 7, 2007.

(51) Int. Cl.
*G06Q 50/00* (2012.01)
(52) U.S. Cl. .................................. 705/2; 705/3
(58) Field of Classification Search .............. 705/2, 3
See application file for complete search history.

(56) References Cited

U.S. PATENT DOCUMENTS

| | | | |
|---|---|---|---|
| 6,578,003 B1* | 6/2003 | Camarda et al. | 705/3 |
| 7,630,788 B1 | 12/2009 | Reese | |
| 2003/0221687 A1 | 12/2003 | Kaigler | |
| 2003/0236681 A1 | 12/2003 | Ninomiya et al. | |
| 2003/0236683 A1 | 12/2003 | Henderson et al. | |
| 2004/0059634 A1 | 3/2004 | Tami et al. | |
| 2004/0260577 A1 | 12/2004 | Dahlin et al. | |
| 2005/0096785 A1 | 5/2005 | Moncrief et al. | |
| 2007/0214009 A1 | 9/2007 | Epstein et al. | |
| 2008/0013705 A1* | 1/2008 | Yoffie et al. | 379/201.12 |
| 2008/0015897 A1 | 1/2008 | Moradi et al. | |
| 2008/0109252 A1* | 5/2008 | LaFountain et al. | 705/2 |
| 2008/0183500 A1* | 7/2008 | Banigan | 705/3 |
| 2008/0228525 A1* | 9/2008 | Weickert et al. | 705/3 |

OTHER PUBLICATIONS

Final Office action for U.S. Appl. No. 11/959,837 dated Nov. 24, 2010.

(Continued)

*Primary Examiner* — Gerald J. O'Connor
*Assistant Examiner* — Neha Patel
(74) *Attorney, Agent, or Firm* — Francis C. Kowalik; Marshall, Gerstein & Borun LLP; Randall G. Rueth

(57) ABSTRACT

A comprehensive medication management system is disclosed. The comprehensive medication management system offers a number of compliance related services that may be offered to patients in to improve medication therapy compliance. The system identifies compliance barriers facing individual patents and recommends services designed to overcome those barriers. The system further provides feedback to patients to document their progress. The system proactively identifies patients who may benefit from compliance services and blocks their transactions until the services are explained. The point of sale block may be expanded to other classes of patients so that the transactions of other classes of patients blocked and other messages delivered or some other customized interactions carried out. The medication management system may serve as a central repository of information about a patient's medication treatment program and the medication management system may provide quick and easy access to a patient's entire medication history to facilitate consultations between a pharmacist and the patient. The medication management system may generate lists of tasks for pharmacists to perform in order to deliver the compliance related services to individual patients.

19 Claims, 28 Drawing Sheets

OTHER PUBLICATIONS

Office action for U.S. Appl. No. 11/959,837 dated May 21, 2010.
Office action for U.S. Appl. No. 11/959,428 dated Nov. 29, 2010.
Final Office action for U.S. Appl. No. 11/959,305 dated Dec. 27, 2010.
Office action for U.S. Appl. No. 11/959,305 dated May 17, 2010.
Final Office action for U.S. Appl. No. 11/959,425 dated Nov. 26, 2010.
Office action for U.S. Appl. No. 11/959,425 dated Jun. 10, 2010.

* cited by examiner

FIG. 5

Walgreens
Rx ComplianceAdvisor    Jay Nadas

Logout | Tips | Help

Central Patient Inquiry    Search  Register/Update  Questions  Services

Search for the patient.

In order to determine which Walgreens services will work best for you, please let us know if you are a patient or a caregiver? ⦿ Patient ○ Caregiver Primary Phone: (847) 252 - 256   Birth Date: 258 / / (MM/DD/YYYY)
First NAme: _____  Middle: ___  Last Name: _____ 260
[Search Patient] [Clear Fields] 254

Search Results

Click on the patient's name to continue or register if not listed.    << Previous  Showing 1-20 of 47  Next >>

| Name | Address | City | Primary Phone | Birth Date | Sex | |
|---|---|---|---|---|---|---|
| DOE, CLARK | 108 WILMOT RD | DEERFIELD | (847) 543-1378 | 01/12/1970 | MALE | Update Info |
| DOE, HENRY | 176 RAND RD | BUFFALO GROVE | (847) 130-9891 | 01/03/1980 | MALE | Update Info |
| DOE, LARRY | 108 BUFFALO GROVE RD | DEERFIELD | (847) 348-1834 | 03/13/1995 | MALE | Update Info |
| DOE, PETER M.D. | 1157 DEERFIELD RD | VERNON HILLS | (847) 284-1844 | 06/15/1979 | MALE | Update Info |
| DOE, VICTORIA | 1938 WAUKEGAN RD | ARLINGTON | (847) 349-3849 | 07/15/1979 | FEMALE | Update Info |

264 [Register New Patient]

266 [Print Blank Questionnaire]

268 ↗    250

Done    Local Intranet

FIG. 6

Contact Information

\* = Required Field
* 1) What is your name? [282] [284] [286] [288]
* 2) Sex? ○Male ○Female ← 290
* 3) What is your primary phone number? [292]
* 4) What is your birthday? [294] (MM/DD/YYYY)
* 5) What is your email address? [296] (john_smith@walgreens.com) 298
* 5) What is your mailing address?
  Address: [ ]
  Zip code: [300]
  City: [302]
  State: [304]

[Back] [Continue] [Cancel]

Walgreens RxComplianceAdvisor    Jay Nadas

Logout | Tips | Help
Search  Register/Update Questions  Services

Question Set for Jane Q.Pubblic

Step 3 of 4: Answer questions.
Thank you. Now, I just have a few more questions to ask you.
Your answers will help me determine how Walgreens can make it easier for you to stay on track with medications. —322

Are you comfortable answering questions on behalf of the patient? ⊙Yes ○No
Great! Now, I just have a few questions to ask.
On a scale of 1 to 7 with 1 being not at all and 7 being definitely - please rate the following issues.

| Question | Not at All | | | | | | Definitely |
|---|---|---|---|---|---|---|---|
| How likely is it that you would discontinue a current medication because of a potential side effect? | ○1 | ⊙2 | ○3 | ○4 | ○5 | ○6 | ○7 |
| How confident are you that Walgreens is truly concerned about your health? | ○1 | ⊙2 | ○3 | ○4 | ○5 | ○6 | ○7 |
| How confident are you that Walgreens is can help you better manage your health? | ○1 | ⊙2 | ○3 | ○4 | ○5 | ○6 | ○7 |
| How difficult is it for you to remember to take your medication(s) as prescribed? | ○1 | ⊙2 | ○3 | ○4 | ○5 | ○6 | ○7 |
| How difficult is it for you to remember to refil your medication(s) on time? | ○1 | ⊙2 | ○3 | ○4 | ○5 | ○6 | ○7 |
| How important is it for the pharmacy to let you know when your prescription is ready? | ⊙1 | ○2 | ○3 | ○4 | ○5 | ○6 | ○7 |
| How likely is it that cost of the prescription will cause you to discontinue - or take less of - your medications? | ○1 | ⊙2 | ○3 | ○4 | ○5 | ○6 | ○7 |
| How likely is it that the person picking up the prescriptions is the same person who takes the prescription? | ○1 | ⊙2 | ○3 | ○4 | ○5 | ○6 | ○7 |

*End of Questions*

[Continue]  [Print Blankn Questionnaire]  [Back]  [Cancel]
  328              330                    332    334

326 (arrow to Not at All)
324 (arrow to row)

File:///R:/Requirements%20and%20Deliverables/Phase%20I/Prototypes/Version%200.13c/static_800_usability/question_set.htm#    Local Intranet

Rx PHARMACY — 408

Personalized Medication management Solutions — 406

*Helping you take charge of your medications™*
This guide is designed to help you determine which Walgreens services could make your pharmacy experience even better!

Prepared for
JANE Q. PUBLIC — 404

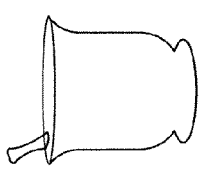

400 / 402 / 410

JANE Q. PUBLIC
200 WILMOT RD
DEERFIELD, IL 60015
01/01/1991   PH(847) 315-4088

Here's your report. It looks like the following services would help make prescription maintenance easier for you. Would you like to enroll in any of these services? We can get you started today!

Auto Fill- — 412

By enrolling in Auto-fill, the scheduling and hassle associated with refilling your maintenance prescriptions is automated such that the only concern remaining is to pick up the medication, and making sure you take it exactly as prescribed. A maintenance medication is one that is prescribed in order to prevent long-term complications associated with a particular ailment.

420

*Basic Medication Tips:* — 422

- Find ways to fit your medication regimen into your daily routine. For example, remind yourself to take your medications after you brush your teeth or while watching the evening news.
- Use device like a pill box, timers, or watches with alarms to help you remember when to take your medications.
- Use a medication dosing calendar or personal log to record when you have taken your medications.
- Always speak with your doctor before you stop taking a medication.
- Learn more about your health condition(s) and the medication(s) you are taking by asking your doctor or pharmacist. The more you know the better you will be at managing your health.

For more information about our great Walgreens services, see the back of this report. Our pharmacists can help sign you up for these sevices at any time! — 424

Here is my contact information should you have questions about this or any other service: — 426
RPh Name: _____
Phone (847) 267 - 0403

Walgreens Services That May Interest You — 430

*Check with your Walgreens pharmacist for more information, or to sign up for these services:*

☒ Auto Refills - AUTOMATICALLY — 432
We can automatically refill your prescriptions before they run out!

☒ Education Sessions — 434
Our pharmacists will help you administer prescriptions safety and effectively.

☒ ExpressPay™ — 436
Have a prescription charged to a credit card number we keep on file.

☐ Pill Box — 438
Our way of helping caretakers and patients alike keep on schedule. — 440

☐ Prescription Pick-Up Notices — 442
Want to know when your prescription is ready for pick-up? We can e-mail you!

☐ W Card Prescription Savings
Can help reduce prescription costs for those with little or no insurance.

Mark the box of a service you wish to activate and drop this off at your local Walgreens.

Note: The marked boxes are currently active services.

_____

Did this service help you? Please send us an email at compadv@walgreens.com and tell us your story.

FIG. 11C

Things to Keep in Mind:
Ways to help with taking your medications include knowing exactly how to take your medications, knowing what the medications are used for, and how they can benefit your helth.

You can make a difference in your health. Take your medicationa as prescribed by your doctor. Speak with your doctor or pharmacist if you have any concerns about your medications.

You Walgreens Pharmacist is always available to discauss ways to help you take your medications correctly.

610

*Use this section for your notes/ questions*

612

Our services that may help you take charge of yourmedications include:

☐ Auto Refills
We can automatically refill your prescriptions

☐ Refill reminder
Know when your prescriptions are ready to be refilled

☐ Education Sessions
Our pharmacists will help you administer prescriptions safely and effectively ☐ W Card patient savings program
Can help reduce prescription costs for those with little or no insurance ☐ ExpressPay
Have a prscription costs for those with little or no insurance ☐ Prescription Pick-Up Notices
Want to know when your prescription is ready for pick-up? We can email you!

☐ Pill Box
One way of helping caregivers and patients alike keep on schedule ☐ Medication Manager
Helping you keep track as you take your medications

Jane Q Public
123 MAIN STREET, LINCOLNSHIRE, IL 60060
10/27/1908    (847) 555-5555

How to use this chart
1. Write in the days of the week
2. On the first day, write in the time of each dose
3. Check off boxes as you take a dose

ACIPHEX 20MG TABLETS — TAKE 1 TABLET BY MOUTH 4 TIMES DAILY AS DIRECTED
Shape: CIRCLE
Color: WHITE

GLIPIZIDE 10MG TABLETS — TAKE 1 TABLET BY MOUTH 3 TIMES DAILY AS DIRECTED
Shape: OBLONG
Color: DARK BROWN

INTAL INHALER — USE 1 INHALATION BY MOUTH 2 TIMES DAILY AS DIRECTED
Shape: INHALER Notes/questions for doctor Notes/questions for pharmacist Side-effects and other comments

FIG. 15

Walgreens - Rx Compliance Advisor - Microsoft Internet Explorer

File Edit View Favorites Tools Help

Address: C:\Eclipse 3.1.2\WebTools\workspace\RXComplianceAdvisor\II\CampaignManagement\CampaignSpecs.html RxComplianceAdvisor  User Name Friday March 2, 2007  Logout Printable Version | Contact Us | Tips | Help Home >> Search Campaign
Step 1: Edit Campaign

Edit Campaign Form

- Name: CAMPAIGN NAME 1 — 902, 904
- Description: Campaign description edhgas a safa f asdf asfda sdfa — 906, 908
- Priority: 12 — 910
- Coordinator: JOHN DOE — 912
- Sponsor: PFIZER — 914
- Fee Structure: FEE STRUCTURE 1 — 916
- Billing Structure: BILLING STRUCTURE 1
- Cost: $251,000.00

- Campaign Status: INACTIVE — 918
- Start Date: (MM/DD/YYYY): 02 / 10 / 2007 — 920
- End Date: (MM/DD/YYYY): 10 / 10 / 2007 — 922
- Expected Result: EXPECTED RESULT — 924
- Coordinator Contact Details: 847-214-4567, john.doe$walgreens.com
- Payor: PFIZER — 928
- Fee: $122.00 — 930
- Silling: BILLING 1 — 932

[Save] [Cancel]

900

Done    My Computer

FIG. 19

*(Screenshot of "Walgreens - Rx Compliance Advisor" Internet Explorer window)*

Advisor Session for JC SEVENTEEN — 1002
Patient information reference

| Name | Address | City | State | Zip Code | Primary Phone | Birth Date | Sex |
|---|---|---|---|---|---|---|---|
| SEVENTEEN, JC | JC STREET | EAGAN | MN | 55120 | (847) 700-0000 | 01/01/1970 | M |

Printable Version | Contact Us | Tips | Help

Thursday June 7, 2007

⚠ Please ask the following questions, 1-7 scale uses 1 as not at all and 7 as definitely - otherwise follow question instructions.

Question

1022 — According to our records, this looks as if it is your first time taking this medication. Is this right?  ○Yes 1026   ○No 1028

1024 — Are you interested in learning more about how to take this medication (including things to monitor, side effects, and the goal of why you take this medication?   ○Yes 1030   ○No 1032

End of questions. Click "Continue" button below.

[Continue] [Cancel]

Walgreens - Rx Compliance Advisor - Microsoft Internet Explorer

File Edit View Favorites Tools Help

Address: file:///X:/GROUPS/Reengnr/RxComplianceAdvisor/Phase%20Three/Requirements/Prototypes/V1.1/html/phaseIII/OnePatientView/OnePatientView_Interaction.html?_exam Thursday March 1, 2007
Printable Version | Contact Us | Tips | Help | Logout

PATIENT SUNDAY
Specialty Patient? YES    RCA Patient? YES

| Name | Address | City | State | Zip Code | Primary Phone | Birth Date | Sex |
|---|---|---|---|---|---|---|---|
| SUNDAY, PATIENT 1114 | 325 OAK CREEK DR | WHEELING | IL | 60090 | (847) 111-2222 | 10/14/2001 | F |

1116   1118   1120

Patient Interactions

Interactions | Drugs | Allergies and Health Conditions | Services

| Rx Number | Drug Name | Last Sold Date | Store |
|---|---|---|---|
| 12345 | LORTAB 7.5MG TABLETS | 12/19/2006 | 32019 |
| 12241 | MERIDIA 10MG CAPSULES | 12/11/2006 | 32020 |
| 12342 | COMBIPRES 0.3MG TABLETS | 10/11/2006 | 32019 |
| 12243 | COMBIPRES 0.2MG TABLETS | 10/09/2006 | 32020 |
| 12344 | LIPITOR 10MG TABLETS | 10/09/2006 | 32019 |
| 12245 | ASA 8MG TABLETS | 10/09/2006 | 32020 |
| 12346 | CADUET 5/20MG TABLETS | 08/11/2006 | 32019 |
| 12247 | SINGULAIR 5MG TABLETS | 08/10/2006 | 32020 |
| 12348 | PENICILLIN G 5,000,000U/VIAL | 08/10/2006 | 32019 |
| 12249 | BIAXIN 500MG TABLETS | 07/10/2006 | 32020 |
| 12340 | LIPITOR 7.5MG TABLETS | 03/26/2005 | 32019 |
| 12045 | ASA 10MG TABLETS | 04/18/2003 | 32020 |
| 11845 | COMBIPRES 1.0MG TABLETS | 04/18/2003 | 32019 |
| | CALCIUM 600 W/ D G/S CAPLETS WALG | 12/21/2006 | 32020 |
| | GARLIC OIL 1500MG CAPSULES W/F | 09/01/2006 | 32019 |
| | GLUCOSAMINE CHONDROITIN DS CAPS W/F | 12/18/2005 | 32020 |
| | VITAMINE E 4001U G/S SOFTGELS WALG | 05/12/2004 | 32019 |

Back    Add New Interaction

PATIENT SUNDAY
Specialty Patient? YES   RCA Patient? YES

| Name | Address | City | State | Zip Code | Primary Phone | Birth Date | Sex |
|------|---------|------|-------|----------|---------------|------------|-----|
| SUNDAY, PATIENT | 325 OAK CREEK DR | WHEELING | IL | 60090 | (847) 111-2222 | 10/14/2001 | F |

Patient Interactions — 1116

[ Interactions ] [ Drugs ] [ Allergies and Health Conditions ] [ Services ]

Current Allergies Include — 1162
- DRAMAMINE 50MG TABLETS
- Shrimp
- Onion

Current Health Conditions Include: — 1164
- No information on file

[ Back ]   [ Add New Interaction ]

PATIENT SUNDAY
Specialty Patient? YES    RCA Patient? YES

| Name | Address | City | State | Zip Code | Primary Phone | Birth Date | Sex |
|---|---|---|---|---|---|---|---|
| SUNDAY, PATIENT | 325 OAK CREEK DR | WHEELING | IL | 60090 | (847) 111-2222 | 10/14/2001 | F |

Interactions | Drugs | Allergies and Health Conditions | Services

The following services are currently active.
- ExpressPay
- W Card Prescription Savings
- Prescription Pick-Up Notices

SYSTEM AND METHOD FOR SELECTING COMPLIANCE RELATED SERVICES

FIELD OF THE INVENTION

The present invention relates to a system for delivering comprehensive medication management services to patients. An embodiment a medication management system includes hardware, software, and pharmacy workflows for identifying patients who may benefit from medication management services, identifying the medication management services most appropriate for individual patients, providing medication therapy compliance feedback to patients, and implementing reimbursable services on behalf of stakeholders in the form of campaigns providing customized interactions with targeted patients and documenting the results.

BACKGROUND

Effective management of a patient's medication therapy is an important factor in achieving successful treatment results. The closer a patient adheres to his or her prescribed medication treatment program, the more likely that the treatment will be effective. Unfortunately, in many instances patients do not adequately comply with their medication therapy programs. Poor compliance with treatment programs can result in negative health impacts for the patient as well as negative impacts on those who have an interest in maintaining the patient's health.

In a typical medication therapy setting there is a number of parties or stakeholders who have an in interest in achieving a successful result. FIG. 1 is a diagram illustrating a number of the stakeholders who may have an interest in a patient's successful medication treatment outcome. At the center is the patient 10. No stakeholder has a greater interest in an effective medication treatment program than the patient 10. Many patients, such as children or the elderly, may have a caregiver 12 who is responsible for caring for them. A caregiver 12 may be responsible for scheduling doctor appointments, transporting the patient to their appointments, getting prescriptions filled, administering medications, and so forth. The doctor 14 treating the patient 10 has a professional interest in the patient's health. The pharmacist 17 who fills the patient's prescriptions also has a professional interest in serving the patient similar to that of the patient's doctor 14. The pharmacy 16 that sells the patient his or her prescribed medications has a business interest in continuing to serve the patient. If the patient is covered by insurance or if the patient is a member of a managed-care organization which pays for some or all of the patient's medications, the insurance company or managed-care organization 18 will have an interest in managing the patient's medications and keeping costs down. At a further remove, the pharmaceutical company 20 that manufactures the patient's medications has an interest in continuing to sell medications to the patient 10. Even more generally, pharmacy trade groups 22, such as the American Pharmacists' Association, The American College of Clinical Pharmacy and others, may have an interest in learning about effective medication therapy management techniques, as well as trends in the industry, successful drug treatments and the like. Similarly, doctors, nurses, hospitals and other members of the broader medical community 214 will have an interest in learning about effective medication therapies, methods of keeping costs down and improved treatment outcomes, as will public health organizations 26 and government agencies 28 tasked with providing health-related services.

Of the stakeholders identified in FIG. 1, only the caregiver 12, the doctor 14, the pharmacy 16 and perhaps the insurance company or managed-care organization 18 are likely to have direct contact with the patient 10. Nonetheless, other stakeholders may wish to obtain data regarding the patient and the patient's medication therapy program. Various stakeholders may also wish to communicate important messages to individual patients regarding their medication treatment programs. What is more, even though the caregiver 12, the doctor 14, the pharmacy 16 and the even insurance company/managed-care organization 18 may have somewhat regular contact with the patient 10, the nature of the relationship with the patient and the frequency of contact with the patient may vary significantly for each entity. For example, the patient is unlikely to discuss specifics of his or her treatment with the insurance company 18. The doctor 14 prescribes the patient's medication but may not have accurate information about the patient's compliance with the prescribed medication therapy, and so forth. Thus, while each stakeholder may be in a position to obtain a limited amount of information about the patient 10 and the patient's medication treatment program, the limited nature of the information results in each party receiving only a partial view of what is actually taking place with regard to the patient's medication therapy.

In many cases, data collected by or known by one stakeholder may be highly valuable to one or more other stakeholders. For example, once a patient's doctor 14 prescribes a specific medication treatment, the doctor has no way of knowing how closely the patient is adhering to the prescribed treatment regimen. The pharmacy, on the other hand, is in a position to review the patient's prescription fill history to determine whether the patient has had enough medication on hand to comply with the prescribed treatment program. Since a patient's failure to comply with his or her doctor's prescribed treatment program could lead to an unsuccessful result, which in turn could lead to a more serious illness and more expensive treatments, many of the stakeholders identified in FIG. 1 will have an interest in knowing whether the patient 10 is complying with his or her prescribed medication therapy.

Although there are many stakeholders who may have an interest in a patient's medication therapy, a successful medication management program must focus on the individual patient. Each individual patient will have unique circumstances that define the medication management issues facing that patient. For example, some patients may have a very complicated medication regimen that is difficult to keep track of and which is nearly impossible to follow without fault. Other patients may have a nonchalant attitude toward their medication which may cause them to frequently miss doses. Still other patients may not have the financial resources to cover the costs of their medications. Some treatments may require frequent tests to ensure the efficacy of the treatment or to detect the presence of adverse side effects. A medication management system must be capable of dealing with all of these factors and more in order to deliver all of the services necessary to help patients manage their medications.

A medication management system is desired that will take into account all of the unique circumstances facing individual patients and provide services uniquely tailored to meet each patient's needs. Such a medication management program must be scalable to meet the individualized needs of hundreds of thousands or even millions of individual patients. Further it is desired that a medication management system may serve as a central repository for information regarding patients and their medication treatment programs. This information may be collected and presented in ways that will help improve patient compliance with their medication treatment programs and facilitate the delivery of compliance related services. It also desired that a medication management system provide a mechanism for identifying patients who may benefit from compliance related services and communicating the availability of such services to such patients. It is also desirable to identify other classes of patients in order to deliver special messages or have other customized interactions with the members of such classes of patients on behalf of various stakeholders having an interest in the various patients' treatment outcomes.

SUMMARY

The present invention provides a comprehensive medication management system. The comprehensive medication management system offers a number of different compliance related services that may be offered to patients in order to improve compliance with their individual medication therapy programs. The medication therapy system helps to identify the personal compliance barriers facing individual patients, and recommends compliance services that are best suited for overcoming a patient's personal compliance barriers. The medication management system further provides feedback to patients to document how their compliance has improved (or not) as a result of the compliance services they are receiving. According to an embodiment, a medication management system may be expanded to provide reimbursable cognitive services to third party stakeholders. Reimbursable cognitive services may include medication therapy management (MTM); insurance benefits communication services; quality assurance programs; medication safety, efficiency and appropriate usage programs; and medication adherence and persistence programs; among others. An embodiment of a medication management system actively identifies patients who may benefit from compliance services and blocks transactions with such patients at the point of sale until a consultation takes place between a pharmacist and the patient in which the benefits of the compliance related services are explained to the patient. The point of sale block may be expanded so that other classes of patients may be identified and their transactions blocked at the point of sale until some other message is delivered or some other customized interaction with the patient takes place. The expanded point of sale blocking feature may be used to implement reimbursable campaigns on behalf of third party stakeholders to reach targeted patients. For example, a third party stakeholder may be willing to pay for a particular message to be delivered to all of a pharmacy's patients taking a certain medication, or to gather information from patients about side effects or some other subject related to their medication therapy.

A medication management system may serve as a central repository of information about a patient's medication treatment program. The medication management system may provide quick and easy access to a patient's entire medication history to facilitate a consultation between a pharmacist and the patient. Additionally, the medication management system may generate lists of tasks for pharmacists to perform in order to deliver the compliance related services that have been offered to individual patients.

Other systems, methods, features and advantages of the invention will be, or will become, apparent to those skilled in the art upon examination of the following figures and detailed description. It is intended that all such additional systems, methods, features and advantages included within this description be within the scope of the invention.

BRIEF DESCRIPTION OF THE DRAWINGS

FIG. 5 is a screen shot of a patient look-up user interface page.

FIG. 6 is a screen shot of a patient contact information user interface page.

FIG. 7 is a screen shot of a patient questionnaire user interface page.

FIG. 10 is a sample medication management printed solutions guide.

FIG. 12 is a sample medication manager chart.

FIG. 15 is a screen shot of a campaign editing user interface page.

FIG. 19 is a screen shot of a campaign question set page.

FIG. 22 is a screen shot of a full screen patient profile user interface page showing a list of patient interactions.

FIG. 23 is a screen shot of a full screen patient profile user interface page showing a list of drugs that have been prescribed to a patient.

FIG. 24 is a screen shot of a full screen patient profile user interface page showing a list of a patient's current allergies and health conditions.

FIG. 25 is a screen shot of a full screen patient profile user interface page showing a list of services a patient is currently receiving.

DETAILED DESCRIPTION

The pharmacy is a significant point of contact between patients and the health-care industry. The present medication management system leverages this relationship to provide additional services to patients for helping the patients manage their medication treatment programs. The pharmacy helps monitor the patient's compliance with his or her medication therapy and provides services for helping patients improve compliance. The medication management system opens lines of communication that run through the pharmacy allowing various stakeholders to interact with patients in a manner previously unavailable.

For purposes of the present disclosure, the pharmacy may be any of the outlets through which the entity implementing the present medication management system sells prescription medications to patients. For example, the pharmacy may comprise a single independent drug store or any one of a number of branch stores in a large drugstore chain. The pharmacy may also be or include a mail-order or on-line pharmacy, and one or more specialty pharmacies dealing in rare expensive medications or drugs that require special administering procedures. Typically, the pharmacy will have a direct relationship with a very large number of patients. Because of the direct relationship between the pharmacy and such a vast pool of individual patients, the pharmacy is ideally placed to provide a number of medication therapy management services of significant value to both the patients and various stakeholders in the medical services delivery community.

Figure 1:
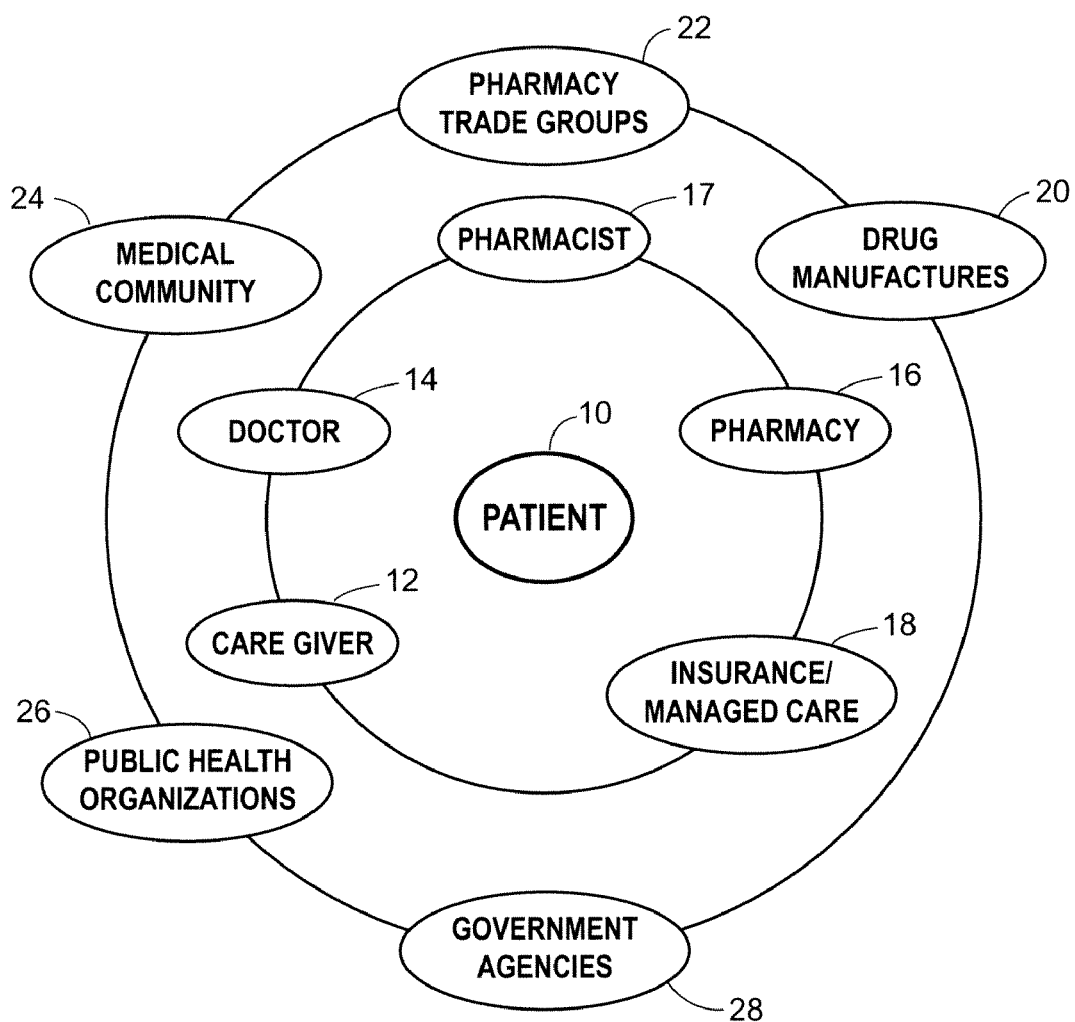
FIG. 1 is a diagram illustrating the various stakeholders having an interest in a patient's medication therapy outcome.
Figure 2:
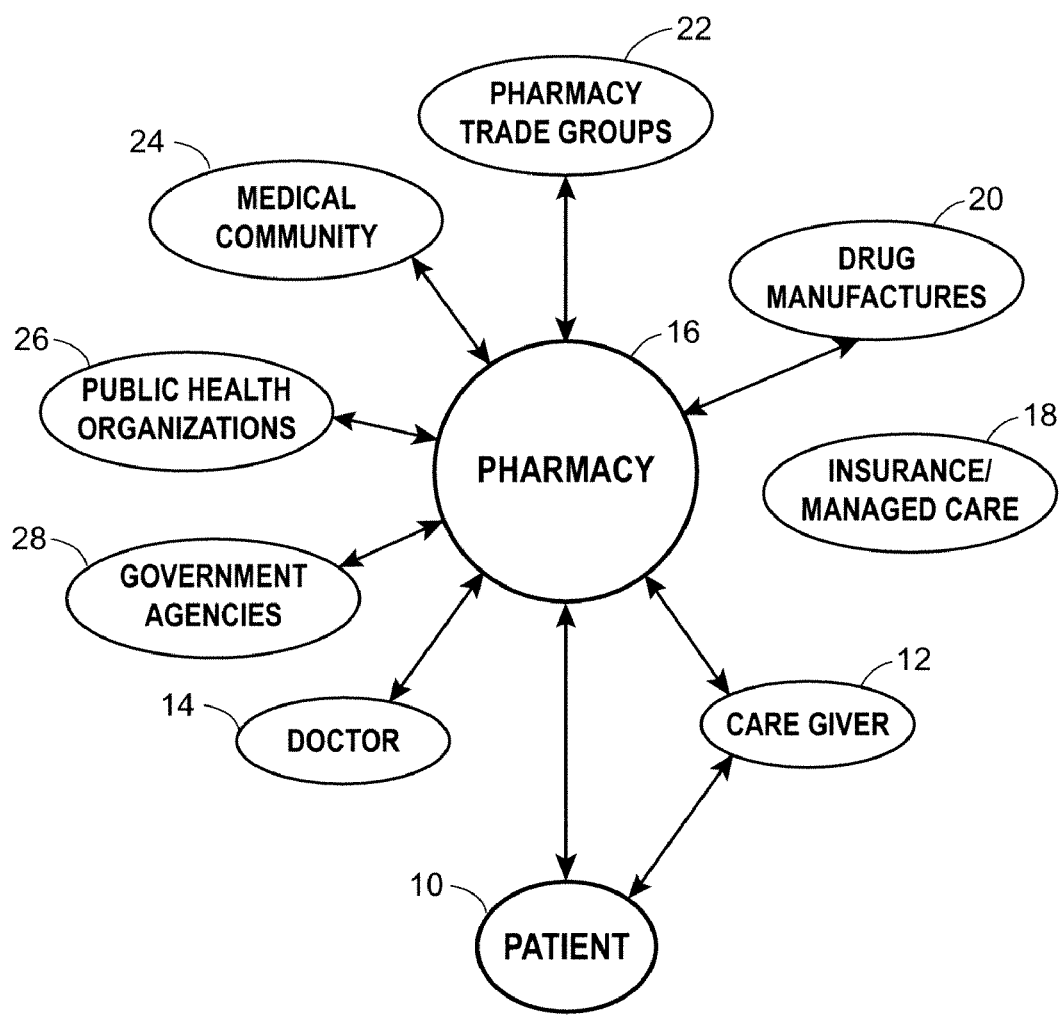
FIG. 2 is a diagram illustrating the communication paths established between the various stakeholders having an interest in a patient's medication therapy outcome and the patient according to an embodiment of a medication management system.

FIG. 2 illustrates the relationships between the various stakeholders and the patient according to an embodiment of a comprehensive medication management system. The medication management system is patient-centric. The medication management system builds on the direct relationship between the pharmacy 16 and individual patients 10 who purchase their medications from the pharmacy 16. Communications between the various stakeholders, including the doctor 14, the insurance/managed-care provider 18; drug manufacturers 20; pharmacy trade groups 22; the larger medical community 24; public health organizations 26; government agencies 28, and the patients 10 are all routed through the pharmacy 16. In cases where a caregiver 12 is present, communications with the patient may be routed through the caregiver 12. Of course, various stakeholders may have additional communications with patients outside the present system (for example, it is assumed that patients will continue to visit their doctors and that important information about the patient's health will be exchanged at those visits), however, within the context of managing the patient's medication therapy through the present medication management system the primary point of contact with the patient 10 is through the pharmacy 16. The various stakeholders may communicate messages to individual patients through the pharmacy 16 and the pharmacy 16 may forward appropriate medication management data back to the various stakeholders. (Appropriate medication management data that may be communicated back to the various stakeholders may include, for example, non-patient specific information, information that an individual patient has agreed may be sent to a specific stakeholder, and so forth. In no circumstances should confidential patient information be sent from the pharmacy 16 to an outside party without the patient's authorization.) Routing communications between the various stakeholders and the patients through the pharmacy 16 allows the pharmacy to control what and how information is passed on to the patient. The pharmacy 16 may create a standardized and systematic approach toward patient communication that ensures that a consistent unified message is delivered to the patient.

Figure 3:
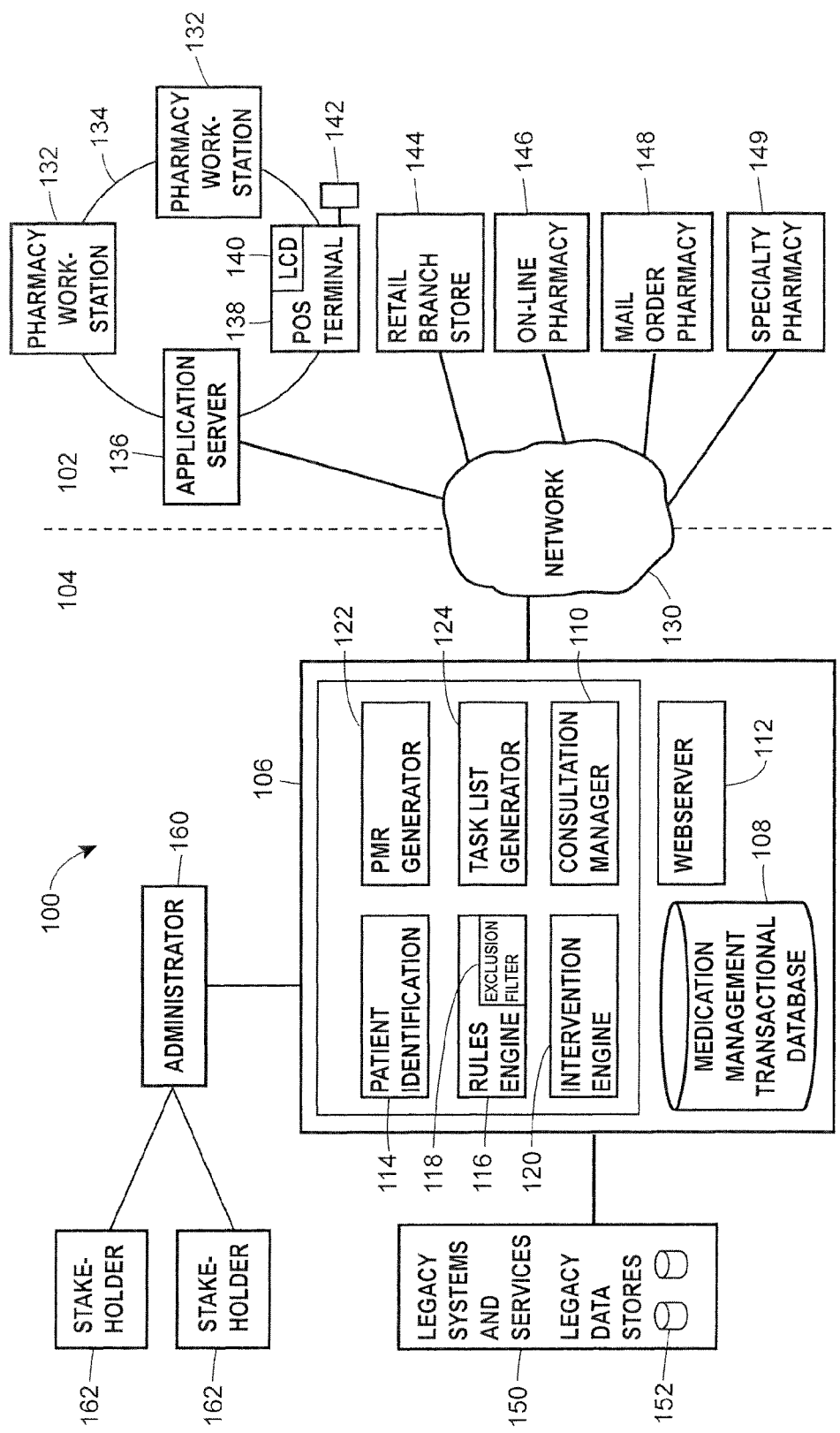
FIG. 3 is a block diagram of an embodiment of a medication management system.

FIG. 3 shows a block diagram of the architecture of an embodiment of a medication management system 100. The systems and processes implemented by the medication management system 100 facilitate the development of individualized medication management programs specially designed to meet the needs of individual patients. Nonetheless, the medication management system 100 may be implemented on a scale that allows any number of individual patients to be enrolled in the medication management system 100. The high-level architecture includes both hardware and software applications, as well as various data communications channels for communicating data between the various hardware and software components. The medication management system 100 may be roughly divided into front-end components 102 and back-end components 104. The front-end components 102 comprise the hardware and software components associated with a pharmacy's sales outlets. For example, a pharmacy may include a number of retail branch stores 144, an on-line pharmacy 146, a mail order pharmacy 148 and a specialty pharmacy 149. The front end components 102 may comprise the hardware and software applications found in each of the pharmacy's retail outlets.

The retail branch stores 144 may include one or more pharmacy workstations 132. The pharmacy workstations 132 may include software applications for managing pharmacy operations, including filling patient prescriptions, and the like. The pharmacy workstations 132 may also include software applications for implementing the present medication management systems. Each store may also include one or more point of sale (POS) terminals 138 for performing cash register functions and certain medication management functions associated with the medication management system 100, as will be described. The POS terminal 138 may include an LCD 140 or other display device for displaying messages to the pharmacist or other pharmacy personnel. (For the remainder of the present disclosure all pharmacy personnel will be referred to as "the pharmacist" even though various tasks within the pharmacy may be performed by personnel who are not registered pharmacists but who operate under a pharmacist's supervision.) The POS terminal may also include a bar code reader 142 for reading bar codes on product packaging and the like. The individual pharmacy workstations 132 and the POS terminals 138 at a particular store may be connected to an in-store local area network 134. The local area 134 network may include an application server 136 which communicates with the backend systems 104 over a wide area network 130. A similar arrangement may be found in the pharmacy's other divisions such as an on-line pharmacy 146, a mail order pharmacy 148, a specialty pharmacy 149, or the like. The wide area network 130 may be a proprietary network, a secure public internet, a virtual private network or some other type of secure network.

The backend components 104 include medication management central processing systems 106 and legacy systems and services 150. The legacy systems and services 150 may include a pharmacy's existing hardware and software systems associated with the delivery of pharmacy services to patients. For example, the legacy systems 150 may execute software applications supporting pharmacy operations, including filling patient prescriptions, keeping track of patients' fill histories, and the like. The legacy systems 150 may also provide ad hoc medication management services that may be integrated into the comprehensive medication management system 100. The legacy systems 150 may include legacy data stores 152 for storing patient information such as the patient's name, address, phone number, insurance carrier, prescription history, and the like, for all patients who have purchased prescription medications from the pharmacy 16.

The medication management central processing systems 106 may include one or more computer processors adapted and configured to execute a number of software applications and other components of the medication management system 100. The central processing systems 106 also include a medication management transactional database 108. The medication management transactional database 108 is adapted to store patient data related to the operation of the medication management system 100. The various applications executed by the central processing systems 106 may retrieve data from and write data to the transactional database 108 and the legacy data stored 152. The applications executed by the central processing systems 106 include a central processing web server 112 and a consultation manager 110. The consultation manager 110 is a web-based tool that assists pharmacists in conducting compliance consultations with patients. The consultation manager 110 interacts with other software components of the medication management system executed by the central processing systems 106 and generates web based interface pages that are distributed to pharmacy workstations 132 by the web server 112 in response to specific URL requests from the pharmacy workstations 132. The central processing systems further include a patient identification module 114; a rules engine 116; an intervention engine 120; a patient medical record generator 122; and a task list generator 124.

Each pharmacy workstation 132 includes a web browser application. The web pages served by the web server 112 are displayed by the web browser applications on the pharmacy workstations 132, providing a graphical user interface by which pharmacists may interact with the medication management system 100. The various web pages forming the user interface may include data pulled from both the medication management transactional database 108 and the legacy data stores 152. The various software applications executed by the central processing systems 106 are responsible for gathering the appropriate data and generating the content included in the user interface pages sent from the web server 112 to the various pharmacy workstations 132. The software applications may be executed on the same computer processor as the web server application 112 or on different computer processors. Furthermore, the medication management system 100 may also rely on software applications executed by legacy systems 150 when legacy software applications provide services and other functionality that are incorporated into a comprehensive medication management program.

As mentioned, the consultation manager 110 is a web based tool for assisting pharmacists in conducting consultations with patients for determining which compliance services should be recommended to individual patients. The patient identification module 114 performs a look-up function for identifying patients who contact the pharmacy and accessing their records and personal data. The rules engine 116 is an application designed to identify the most appropriate services to be recommended to patients based on the patient's answers to questions posed by the pharmacist during a consultation session. The personal medical record (PMR) generator 122 pulls together patient data from multiple different data sources in order to generate a comprehensive view of a patient's medical profile. The data collected by the generator 122 may be used to support a PMR service in which a patient is provided with a printed version of their PMR each time they have a prescription filled.

The intervention engine 120 defines rules for identifying patients to be blocked at the point of sale when they have their prescriptions filled. Patients may be blocked at the point of sale so that some action relating to their medication therapy may be taken before the transaction is complete. The action to be taken may compromise delivering a message to the patient, scheduling a consultation or some other type of appointment, asking questions and getting feedback from the patient, or the like. When a patient is blocked at the point of sale, the transaction may not be completed until the particular task is completed. Finally, the task list generator 124 is responsible for generating lists of tasks to be performed by pharmacists at various facilities operated by the pharmacy 16. Tasks may include contacting individual patients who have signed up for personal refill reminders, preparing automatically refilled prescriptions, scheduling patient consultations, and the like.

The medication management system back-end systems 104 may further include one or more administrator workstations 160. An administrator workstation 160 allows an authorized user (an administrator) to access the various applications running on the central processing systems 106 to alter or adjust the operation of the medication management system 100. For example, one or more stakeholders 162 may wish to institute an educational campaign in which they deliver an educational message to a certain class of patients. The stakeholders 162 may contact the administrator and describe the various characteristics of the patients the stakeholder would like to reach. The administrator may then access the central processing systems 106 via the administrator workstation 140 and alter the rules implemented by the intervention engine 120 for identifying patients who are to be blocked at the point of sale when their next prescription is filled. Alternatively, various processes may be automated such that the stakeholders 162 may define their own set of intervention rules or provide their own list of patients who are to be contacted during a campaign.

A patient profile may be created for every patient participating in a medication management program. A patient profile is an assemblage of all of the data related to managing the patient's medication therapy. Patient profiles may be created by the pharmacy's legacy systems 150 and stored in the legacy data stores 152, with associated medication management data stored in the medication management transactional database 108. Alternatively, the patient profiles may be created as needed in the central processing systems 106 from data pulled from both the legacy systems data stores 152 the central processing systems' transactional database 108. For example, the central processing systems 106 may pull basic patient information, such as the patient name, address, phone number, insurance group number, prescription fill history, and the like from the legacy systems data stores 152. Additional data relating specifically to the patient's medication management program such as the services the patient is currently receiving, the patient's consultation history, messages to be conveyed to the patient, status and alert flags, and other data may be pulled from the medication management transactional database 108.

An important component of an effective medication management program is compliance. The overarching goal of any medication management program is to ensure that patients are consistently taking their medications as prescribed by their doctors. When a patient is not complying with his or her medication therapy the reasons for the patient's non-compliance must be determined so that corrective steps may be taken. There are many different factors that may impact an individual patient's compliance with his or her medication therapy. Sorting out a complex medication regimen and adhering to it can be a significant barrier. Patients taking several different maintenance medications may have difficulty keeping track of which medications they have already taken, when different medications are supposed to be taken and so forth. Another compliance barrier may be cost. If a patient is uninsured or is having difficulty meeting his or her co-payment requirements, compliance may suffer. Indifference may also be a factor. A patient may not believe that strict adherence to his or her prescribed treatment plan is important and may inadvertently miss doses out of sheer apathy. These are but a few examples of the many different factors that may impact an individual's compliance with his or her medication therapy.

A pharmacy may implement services designed to help individual patients improve compliance with their medication therapies. Such services may be introduced on an ad hoc basis or as part of a comprehensive medication management program. A comprehensive medication management program may include implementation of a medication management system such as the medication management system 100 shown in FIG. 3. A comprehensive medication management program may incorporate a pharmacy's existing compliance related services as well as those made available only through the medication management system 100. Compliance related services may include automatic prescription refills for maintenance medications (Auto-Refill); regularly scheduled patient consultations with a registered pharmacist; preparing customized dose charts indicating when each dose of a patient's medications is to be taken; express payment services for automatically charging prescription charges to a patient's credit card or other account (Express Pay); pill-box services for helping patients organize their medications, including electronic "smart pill boxes"; special compliance packaging where all of a patients medications are packaged in combined multi-dose packets; pill box counseling; special re-fill reminders printed on medication labels; a prescription ready and refill reminder alert service for informing patients when their prescriptions are ready and when their prescriptions are due to be refilled (prescription refill reminder and prescription ready messages may include text messages, email messages, personal calls from a registered pharmacist, automated calls, or calls from a central call center); a redirect service to redirect reminder messages to a designated caregiver; a discount program in which qualified patients can sign up for prescription discounts; a frequent prescriber program; a script alignment service for patients taking multiple medications so that all of their prescriptions may be filled at the same time to avoid multiple trips to the pharmacy; a health information card, and so forth.

Auto refill is a service provided for patients whose maintenance medications must be refilled on a periodic basis. The pharmacy's legacy systems 150 keep track of each patient's prescriptions and when they are due to be refilled. The legacy systems 150 may perform a batch process on a periodic basis to review the prescription records of all of the pharmacy's patients who have signed up for the auto-refill service to determine which prescriptions must be refilled during an upcoming period. For example, a batch process may be performed every weekend to determine which prescriptions are due to be refilled during the upcoming week. The prescriptions that must be filled during the upcoming period are assigned to various pharmacists who are tasked with preparing the various prescriptions. When the refill prescriptions are ready the patients may be contacted over one or more preselected communication channels to notify them that their prescriptions are ready to be picked up. For example, patients may be notified by e-mail message, SMS text message, automated phone message, a telephone message from a live agent at a central call center, or a telephone message from a pharmacist at the nearest branch store where the patient can pick up his or her refilled prescription. Alternatively, the refilled prescription may be delivered directly to the patient.

A similar refill reminder service may be available for patients who opt not to participate in the auto-refill service, or whose insurance plan does not allow automatic refills, or who live in states where automatic refill services are prohibited. Like the auto-refill service, a batch process may be performed on a regular basis to identify patients who have prescriptions that are due to be refilled during an upcoming period. Reminder messages may be sent to the identified patients over designated communications channels. Again, refill reminder messages may be sent via e-mail or SMS text message, an automated telephone message, a telephone call from a live agent at a central call center, or a live message from a pharmacist at the branch store in the patient's neighborhood. Refill reminder messages may be provided on a number of different occasions. For example, reminder messages may be sent proactively or retroactively. A proactive refill reminder may be sent to the patient several days (e.g., 3 days) before a prescription is due to be refilled. A retroactive reminder message may be sent if a prescription refill is several days overdue (e.g., 7 days). Another reminder message could be sent midway through a patient's medication therapy, reminding the patient to complete the entire course of treatment to ensure the best treatment results.

Compliance packaging is a service that can help patients follow a complex medication regimen. Multiple medications that must be taken together at the same time of day may be packed together in individual packets. For example consider a patient taking three separate medications. The instructions for taking the first medication are to take one pill three times daily. The instructions for taking the second medication are to take one pill twice daily. The instructions for taking the third medication are to take one pill once a day. The patient's medication may be packaged in morning, afternoon, and evening packets. A morning packet may include one pill each of the first and second medications. The noon packet may contain one pill each of the first and third medications. The evening packet may again contain one pill each of the first and second medications. Individualized compliance packaging can be implemented to conform specifically to an individual patient's medication regimen.

A medication manager service may provide a patient with a weekly or monthly dose chart. Each day represented on the chart may include a check box for each dose of the patient's medication that the patient must take during the course of the day. The patient may keep track of his or her medication by checking off the appropriate check box each time he or she takes a dose of his or her medication.

A pill box training service may be offered to patients to provide counseling for setting up their own pill box system. Such counseling may be provided face-to-face by a registered pharmacist and may be customized specifically to the patient's particular medication regimen. Alternatively, special face-to-face counseling sessions may be mandated for all first time fills on maintenance medications and on the first refill.

A prescription alignment service may be provided so that all of a patients prescriptions are arranged so that they will all come due for a re-fill at substantially the same time. Upon implementing the script alignment service, a patient may receive a reduced fill on some medications so that all of his or her medications will become due on the same date. Once this "alignment" date has been reached, all of the patient's prescriptions may be filled on the same day with the same number of days' supply of each medication so that each prescription will again come due for a refill on the same date thereafter. The alignment date may be determined by the date that is the earliest that all medications may be aligned, or a date may be chosen that would incur the least co-payment liability based on the patient's insurance plan. Alternatively, some custom alignment plan may be devised.

A frequent prescriber plan may be instituted to help defray the cost of prescription medications. Under such a program each prescription refill may be recorded. After a certain number of refills (e.g., 10 or 11) the next refill may be subsidized by the pharmacy, or the pharmacy may cover the cost up the patient's insurance co-payment, or some other cost savings measure may be implemented.

According to other compliance enhancement services, special refill reminders may be printed on the labels of maintenance medications. A redirection of reminder service may redirect automated or personal reminders from the patient to a designated caregiver, either temporarily or permanently. Electronic pill counters or electronic pill boxes may be issued to patients to further assist them in keeping track of their medications.

These are but a sampling of the types of compliance related services that may be offered by a pharmacy as part of a comprehensive medication management program. Other compliance services may be included in addition to or instead of those mentioned above in order to provide a comprehensive medication management program that meets the needs of the pharmacy's patients.

Since each patient faces different compliance barriers, the appropriate services for improving a patient's compliance will differ from one patient to another. Therefore, a first step in creating an individualized medication management program is to determine exactly what are the most significant compliance barriers facing the patient. Only after a patient's compliance barriers are known may the appropriate services be suggested for overcoming those barriers.

According to an embodiment of a medication management system, a patient's participation in a medication management program begins with a consultation between the patient and a registered pharmacist. The purpose of the consultation is to identify the patient's personal compliance barriers and to select those pharmacy services most likely to help the patient surmount those barriers. According to the medication management system 100, the consultation manager 110 provides a web based tool to assist the pharmacist in conducting the initial compliance consultation. The consultation manager records the results of the consultation and recommends appropriate services for improving the patient's overall compliance. The consultation manager may also take steps to implement the various compliance services that have been agreed upon between the pharmacist and the patient during the consultation.

Figure 4:
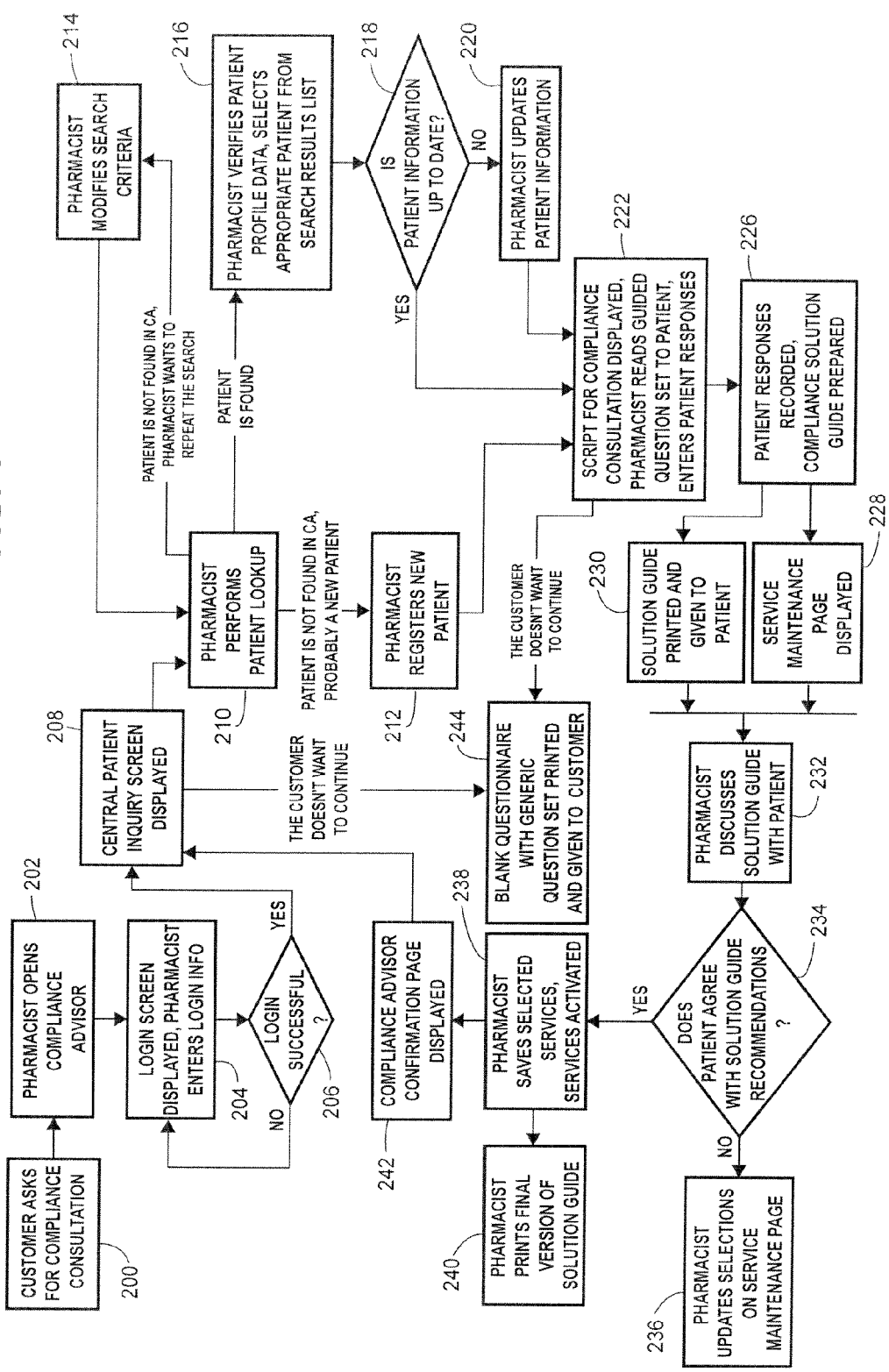
FIG. 4 is a flow chart showing the process flow of a patient consultation with a pharmacist for purposes of identifying appropriate compliance services recommendations for the patient.

FIG. 4 is a flowchart showing the process flows for selecting pharmacy services for a patient enrolling in a medication management program. The process begins at 200 when the patient learns of the program and visits or otherwise contacts the pharmacy. The patient may learn of the program through advertising, on the recommendation of their doctor, through word of mouth, and the like. Alternatively, the pharmacy may make the determination that the patient would benefit from compliance services and may recommend the medication management program to the patient when the patient visits the pharmacy to have his or her prescription filled. In any case, when the patient expresses an interest in enrolling in the medication management program, the pharmacist accesses the medication management system at 202 using a pharmacy workstation 132. When first accessing the medication management system the pharmacist is presented with a login screen at 204. The pharmacist enters an appropriate login name and password, or performs some other identity authentication process. If the pharmacist's login attempt is determined to be unsuccessful at 206 process flow returns to 204 where the login screen is again displayed by the pharmacy workstation's web browser and the pharmacist can continue to enter a login name and password until the pharmacist's login is successful. Once the pharmacist successfully logs onto the system the process flow moves on to 208.

At 208 the medication management web server 112 sends a patient inquiry page to the pharmacy workstation 132. A sample patient inquiry page 250 is shown in FIG. 5. The patient inquiry page 250 includes a number of search fields such as phone number 252, birth date 254, first name 256, middle initial 258, and last name 260 that can be used to search for the patient's profile. The patient inquiry page 250 further contains a button 264 for registering a new patient and a button 266 for printing a generic patient questionnaire. If at any time during the consultation process the patient does not want to continue the consultation, the pharmacist may select the Print Blank Questionnaire button 266 to print a paper version of a patient questionnaire as indicated at 244 in FIG. 4. The questionnaire may be given to the patient who may fill out the questionnaire and return it to the pharmacy at a later time rather than continuing the face-to-face consultation with the pharmacist. Otherwise, the pharmacist may perform a patient lookup at 210 by entering the appropriate data into one or more of the patient search fields of the patient look up page 250. The data entered in various search fields are sent back to the central processing systems 106 where the patient identification module 114 searches the legacy data stores 152 for patient profiles that match the entered search criteria. Patient's whose profile data meet the search criteria are sent back to the pharmacy workstation 132. Search results 268 are shown in the bottom half of the patient inquiry page 250.

If, upon an initial search, the patient's profile does not appear in the search results 268, the pharmacist may alter the search criteria at 214 in a continued effort to locate the patient's profile. If the patient's profile still cannot be found, it is likely that the patient is a new patient who has never been registered with the medication management system 100 or with the pharmacy's legacy systems 150. In this case the pharmacist may select the Register New Patient button 264 to initiate the process of registering the new patient. Selecting the register new patient button 264 causes the medication management web server 112 to send a new patient registration page to the pharmacy workstation 132 to be displayed for the pharmacist. A sample new patient registration page 280 is shown in FIG. 6. The new patient registration page 280 includes a plurality of blank data fields for entering new patient data. For example, the new patient registration page 280 includes fields for entering the new patient's name (first 282, middle initial 284, last 286, and suffix 288); the patient's sex 290; phone number 292; birthdate 294; email address 296, and mailing address (street address 298, zip code 300, city 302 and state 304). The pharmacist enters the patient's data and selects the continue button 306. The new data is sent back to the central processing systems 106 where a new patient profile is created and stored in the legacy data stores 152. Once the new patient has been registered at 212, the process moves on to 222 where the pharmacist begins the patient consultation.

Returning to 210, if the patient profile is found in the search results list 268 on the patient inquiry page 250, the process moves on to 216 where the pharmacist verifies the profile information with the customer and selects the appropriate patient profile from the search results list 268. The patient's profile data are displayed on the pharmacy workstation 132. At 218 a determination is made whether the information in the patient profile is up to date. If the customer information is up to date at 218, the process moves on to 222. If the customer information is not up to date, the pharmacist updates the patient information at 220 before the process moves on to 222.

The patient consultation begins in earnest at 222. The consultation comprises a series of guided questions that the pharmacist asks the patient in order to learn what are the most significant compliance barriers facing the patient. The patient may answer the questions according to a sliding scale such as the 7 point readiness ruler commonly used in the pharmacy industry. Using the 7 point readiness ruler, a patient answers each question with a number from 1 to 7. A lower number represents a less significant compliance barrier and a higher number represents a more significant compliance barrier. Other scales such as a 1-5 point scale or a 1-10 point scale may be employed if more or less resolution in the patient's answers is desired. The set of questions posed to the patient may be dynamic in nature, in that the questions asked during the course of the consultation may depend on answers the patient has given to earlier questions. The questions that the pharmacist asks during the consultation are generated by the consultation manager 110 and are sent to the pharmacy workstation 132 by the medication management web server 112 where they are displayed for the pharmacist by the pharmacy workstation's web browser. FIG. 7 shows a sample user interface page 320 including a portion of the question set that the pharmacist asks the patient during the course of a patient consultation. The user interface page 320 includes a short introductory paragraph 322 that the pharmacist may read to the patient explaining how the consultation will proceed. A first group of eight questions 324 is shown in the sample interface page 320. Each question has a corresponding response scale 326. The pharmacist reads each question to the patient and asks the patient to respond with a number from 1-7. The pharmacist records the patient's responses by selecting the appropriate radio button in the corresponding response scale 326. The user interface page 320 further includes a Continue button 328 a Print Blank Questionnaire button 330, a Back button 332 and a Cancel button 334. When the pharmacist selects the Continue button 328, the patient's responses to the questions 324 listed on the user interface page 320 are sent by the pharmacy workstation 132 back to the web server 112 over the network 130. The consultation manager 110 records the patient's answers in the transactional database 108 and they become part of the patient's profile. Selecting the Print Blank Questionnaire button 330 again causes the pharmacy workstation 132 to print a blank version of the initial consultation questionnaire which the patient may take home and complete and return to the pharmacist at a later time. Upon receiving the completed questionnaire, the pharmacist may enter the patient's answers into the user interface pages associated with the initial consultation in order to record the patient's responses. The Back button 332 returns the interface to a previously displayed page without recording the patients responses to the questions 324. Finally, the Cancel button 334 is provided for ending a consultation if the patient decides not to continue. Selecting the cancel button 334 may return the pharmacist to the patient look up page 250 (FIG. 5) or some other interface page.

Returning to FIG. 4, if at any time during the consultation 222 the patient does not want to continue, the pharmacist may print a blank questionnaire to be given to the patient at 244. Alternatively, if the patient does not want a copy of the questionnaire, the pharmacist may simply cancel the consultation without printing the questionnaire. However, if the patient and pharmacist complete the questionnaire, the patient's responses are recorded at 226 and the rules engine 116 proceeds to determine the compliance services best suited for improving the patient's compliance.

The rules engine 116 maps the questions from the patient questionnaire to various compliance services offered by the pharmacy. The rules engine 116 takes into account the patient's answers to each question (1-7 on the readiness scale) as well as the clinical significance of the services to which each question is mapped. For example, assume that a first question maps to a first service, and a second question maps to a second service. If the patient answers the first question with a higher number on the readiness scale than the second question, the first service to which the first question is mapped will take precedence. However, if the patient answers both questions with the same number, the clinical significance of each service is considered. If the second service has a higher clinical significance, the second service prevails. Alternatively, each question may be weighted. In this case, the patient's numeric response to a question and the question's weight may be considered in determining the significance of the service to which a question is mapped. For example, if a first question has a weight of 2 and a second question has a weight of 3 and the patient responds to each question with a 5, the weighted response to the first question is 10 and the weighted response to the second question is 15, then the service to which the second question is mapped will be given greater significance.

The rules engine 116 may include an exclusion filter 118 which identifies services that are not available for certain patients. A particular insurance plan may not support one or more services offered by the pharmacy. Some states may not allow certain services (such as Auto-Refill for example). Only certain drugs may be eligible for some services. Services should not be offered to patients living in states in which the services are prohibited, or to patients whose insurance plans will not allow the services, or if the patient's medication is not on the list of eligible drugs for a particular service. Once the services have been ranked according to the patient's responses to the questions on the questionnaire and their clinical significance, they are run against the exclusion filter. The exclusion filter will block services from being recommended to the patient if the patient belongs to an insurance plan that disallows the service, or if the branch store is located in a state that prohibits the service, or if the patient's profile indicates that the patient lives in a state that prohibits the service, or if the patient's medication is not on the list of drugs eligible for the service. Those services that are not excluded may be recommended to the patient. Preferably only a limited number of services will be recommended to the patient. For example, perhaps only the 2 or 3 highest ranking services not blocked by the exclusion filter may be recommended to the patient by the rules engine 116.

Figure 8:
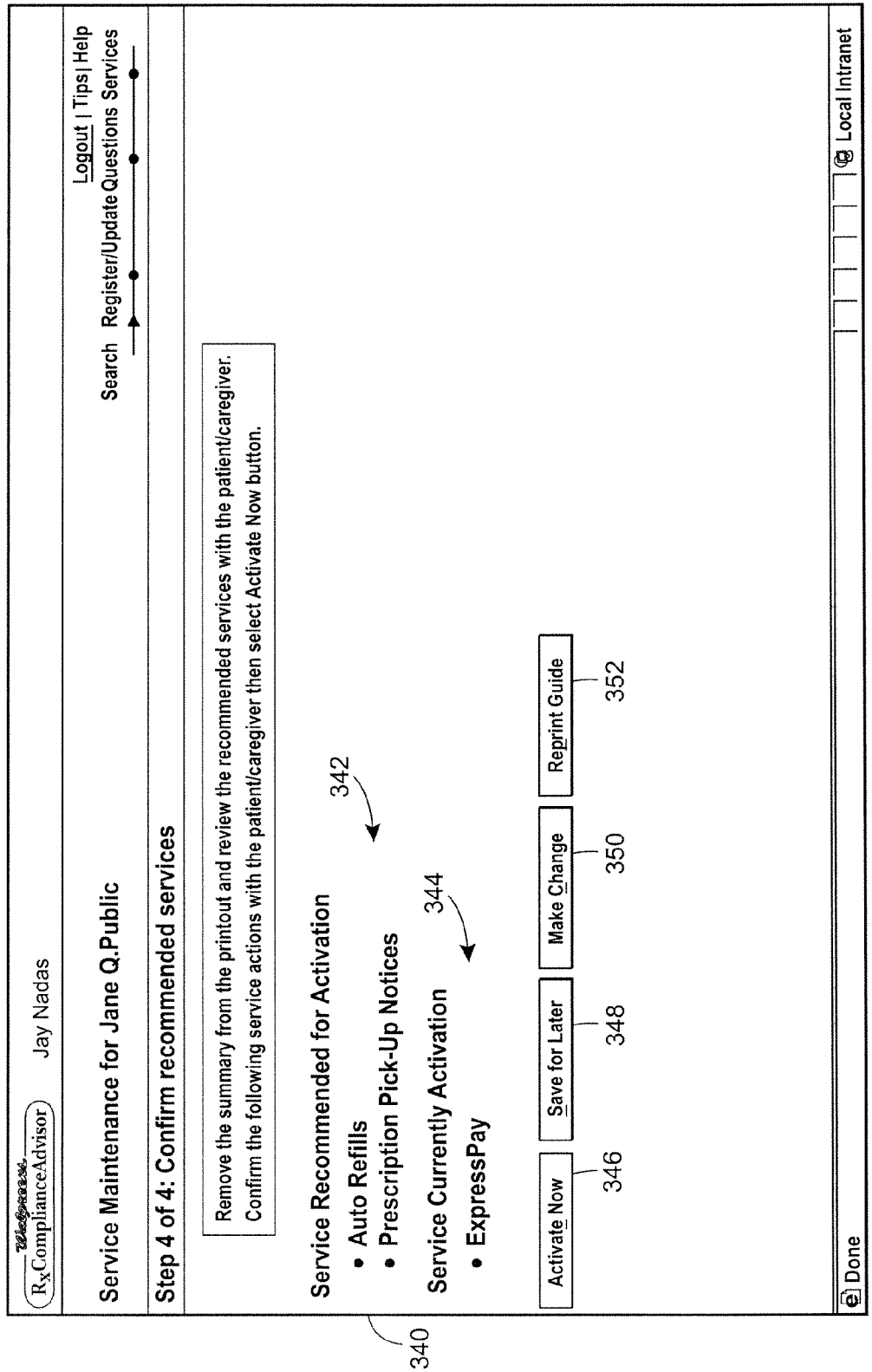
FIG. 8 is a screen shot of a first service maintenance user interface page.

Once the rules engine 116 has determined which compliance services are most appropriate for the patient, the consultation manager 110 generates a service maintenance page. The web server 112 forwards the service maintenance page to the pharmacy workstation 132 where it is displayed by the pharmacy workstation's web browser. FIG. 8 shows an example of a first service maintenance page 340. The service maintenance page 340 includes a list 342 of the compliance services recommended for the patient and a list 344 of services that the patient is already actively receiving. The service maintenance page 340 further includes an Activate Now button 346 by which the pharmacist may activate the recommended services on behalf of the patient. A Save For Later button 348 saves the patient recommendations but does not activate the recommended services. When the pharmacist selects the Save For Later button 348, a pharmacist may retrieve the patient recommendations and activate the services, or change the recommendations at a later time. A Make Change button 350 accesses a second service maintenance page in which the pharmacist may make changes to the services that will be activated on the patient's behalf. Finally, a Reprint Guide button 352 allows the pharmacist to reprint the patient's medication management solutions guide once the final set of compliance services has been selected and the services activated for the patient.

Figure 9:
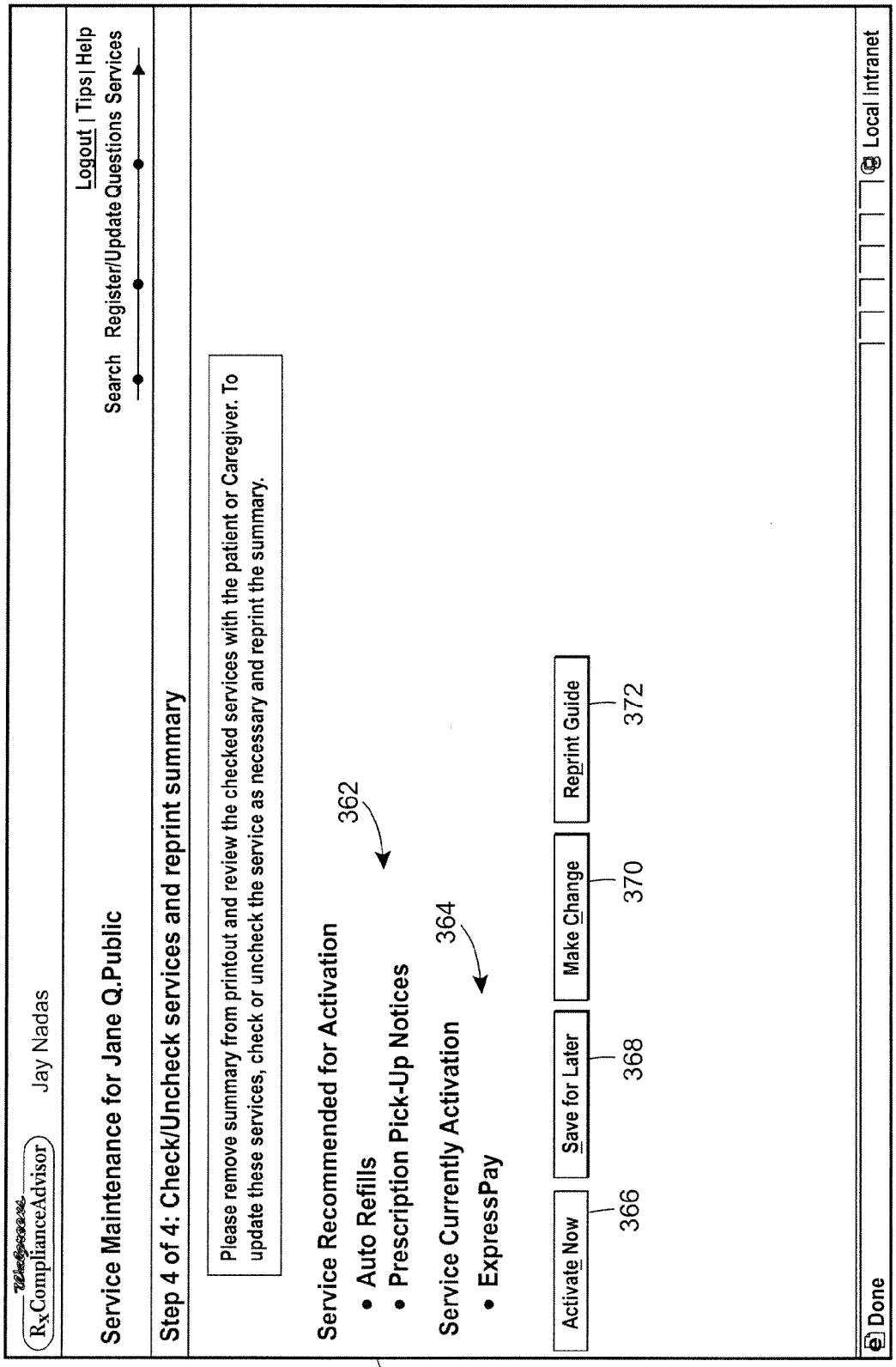
FIG. 9 is a screen shot of a second service maintenance user interface page.

FIG. 9 shows an example of a second service maintenance page 360 for changing a patient's compliance services selections. The second service maintenance page 360 includes a list of active services 362 and a list of the other compliance services 364 offered by the pharmacy. Check boxes are provided adjacent each listed service for selecting or de-selecting the corresponding service. Currently active services and the services recommended by the Rules Engine 116 appear with their corresponding check boxes already selected. The pharmacist may make changes, selecting additional services or de-selecting services that have already been selected, by simply mouse-clicking the appropriate check box 366. Selecting the Submit Changes and Print Guide button 368 saves any changes made to the patient's service selections, activates or deactivates any services as required, and causes a new solutions guide to be printed reflecting any changes made to the patient's active services. The Back button 370 causes the interface to return to a previously displayed page and the Cancel button 380 ends the consultation without any changes being made to the patient's active services.

Returning to FIG. 4, in addition to the service maintenance pages 340, 360, the web server 112 may also forward the compliance services recommendations to the pharmacy workstation 132 in a printable format at 230. The pharmacist may print the printable version of the recommendations for the patient's review and use the printed version to guide the discussion as the pharmacist explains the different compliance services to the patient and explains the reasons why particular services were recommended. At 234 the pharmacist determines whether the patient agrees with the service recommendations and whether the patient wants to sign up to receive the recommended services. If so, the pharmacist saves the recommendations at 238 and the central processing systems 106 take the necessary steps to implement the recommended services on the patient's behalf. Otherwise, if the patient does not agree with the recommended service selections at 234, the pharmacist may make adjustments to the selected services described above. Once the appropriate services have been selected, saved, and implemented, the pharmacist may print the patient's personal compliance solution guide at 240. The personal compliance solution guide identifies and describes the various compliance services that have been activated for the patient. A confirmation page is displayed by the pharmacy workstation's web browser and the pharmacist confirms the patient's compliance service selections at 342. After confirming the patient's selections, the process returns to 208 where the patient inquiry screen is displayed on the pharmacy workstation 132, allowing the pharmacist to perform a patient lookup for the next patient.

FIG. 10 shows an example of a personalized solution guide 400. The solution guide 400 may be printed in a columnar format on two sides of a single sheet of paper so that the solution guide may be folded in half to form a convenient four page brochure style document. The personal solution guide includes a cover page 402. The cover page 402 includes the patient's name 404 and a title 406 identifying the document as the patient's Personalized Medication Management Solution Guide. The title page may also include the name of the pharmacy 408 offering the compliance services outlined in the solution guide 400. The second page of the solution guide 400 is a summary page 410. The summary page 410 includes summaries of the compliance services that have been selected and implemented on the patient's behalf. As can be seen in FIG. 10, the patient Jane Q. Public 404 is enrolled in the Auto Fill service 412 and Text Message Refill Reminder Service 414. The third page of the solution guide 400 is a compliance suggestion page 420. The compliance suggestion page 420 includes basic tips 422 for staying in compliance with one's medication therapy. A short paragraph 424 at the bottom of the compliance suggestion page 420 indicates that additional service offerings are listed on the final page of the solution guide 400. The compliance suggestion page 420 further includes a block 426 where the pharmacist who conducted the consultation with the patient can add his or her personal contact information. As indicated, the final page of the solution guide 400 includes a comprehensive list 430 of the compliance services offered by the pharmacy. The solution guide may be printed with check marks next to the services that have already been selected for the patient. The list of compliance services found on the final page of the solution guide is substantially the same as the list of services 342 displayed on the second service maintenance page 360 of FIG. 9. However, the list displayed for the pharmacist on the service maintenance page may be more comprehensive, including services that may be hidden from the patient's view.

Once a patient completes a consultation with the pharmacist and the recommended compliance services have been implemented, it is desirable to track the patient's compliance in order to determine whether the selected programs have had an effect on improving the patient's compliance, or whether additional or different services should be recommended to the patient to further improve the patient's compliance.

Patient feedback is itself a powerful tool for improving compliance. The medication management system 100 may be adapted to periodically generate a "compliance report card" for the patients participating in a medication management program. Returning briefly to FIG. 3, in order to prepare a compliance report card for a particular patient the central processing systems 106 may pull data such as a patient's prescription fill history from the pharmacy's legacy data stores 152 and medication management data from the medication management transactional database 108. These data may be used to create a report that evaluates the patient's compliance with his or her medication therapy program over a specific period of time. For example, a first compliance report card may be generated 90 days after a patient has had an initial compliance consultation with a pharmacist and subsequent report cards may be generated every six months thereafter. The first report card may cover a six month period beginning three months before the initial consultation and ending three months after the consultation in order to show whether the consultation with the pharmacist and the compliance services implemented as a result of the consultation have had a positive effect. A patient's compliance report card may be generated by the central processing systems 106 and forwarded to a pharmacy workstation by the medication management web server 112. The report card may be printed by the pharmacist when the patient contacts the pharmacy on a date following the date on which the report card is scheduled to be issued. Alternatively, the report card may be generated automatically on the scheduled date and emailed to the patient, faxed, sent by regular mail, posted on a secure website which may only be accessed by the patient, the patient's caregiver, the patient's physician, or some other authorized party, or otherwise distributed to the patient.

Although a patient's compliance report card may be scheduled to be generated on a specific date, the report card need not actually be generated until it can be delivered to the patient. For example, the report card may not actually be generated until the patient contacts the pharmacy to get his or her prescriptions refilled after the date on which the report card is to be issued. On the date the report card is to be issued, a flag may be set in the patient's profile indicating that the compliance report card is due. The next time the patient contacts the pharmacy and the pharmacist performs a patient look up on the patient as described above, the central processing systems 106 will see that the generate report card flag is set and will take the necessary steps to pull the appropriate data and assemble the patient's compliance report card. Once assembled, the web server 112 sends the final document to the pharmacy workstation 132 where the pharmacist may print the report card and discuss its contents with the patient. Of course in other situations, such as when patients use online or mail order pharmacy services, it may be necessary to generate the patient's compliance report card on a date certain and forward it to the patient automatically over an appropriate communication channel, such as via email, a secure website, or the like.

Figure 11A:
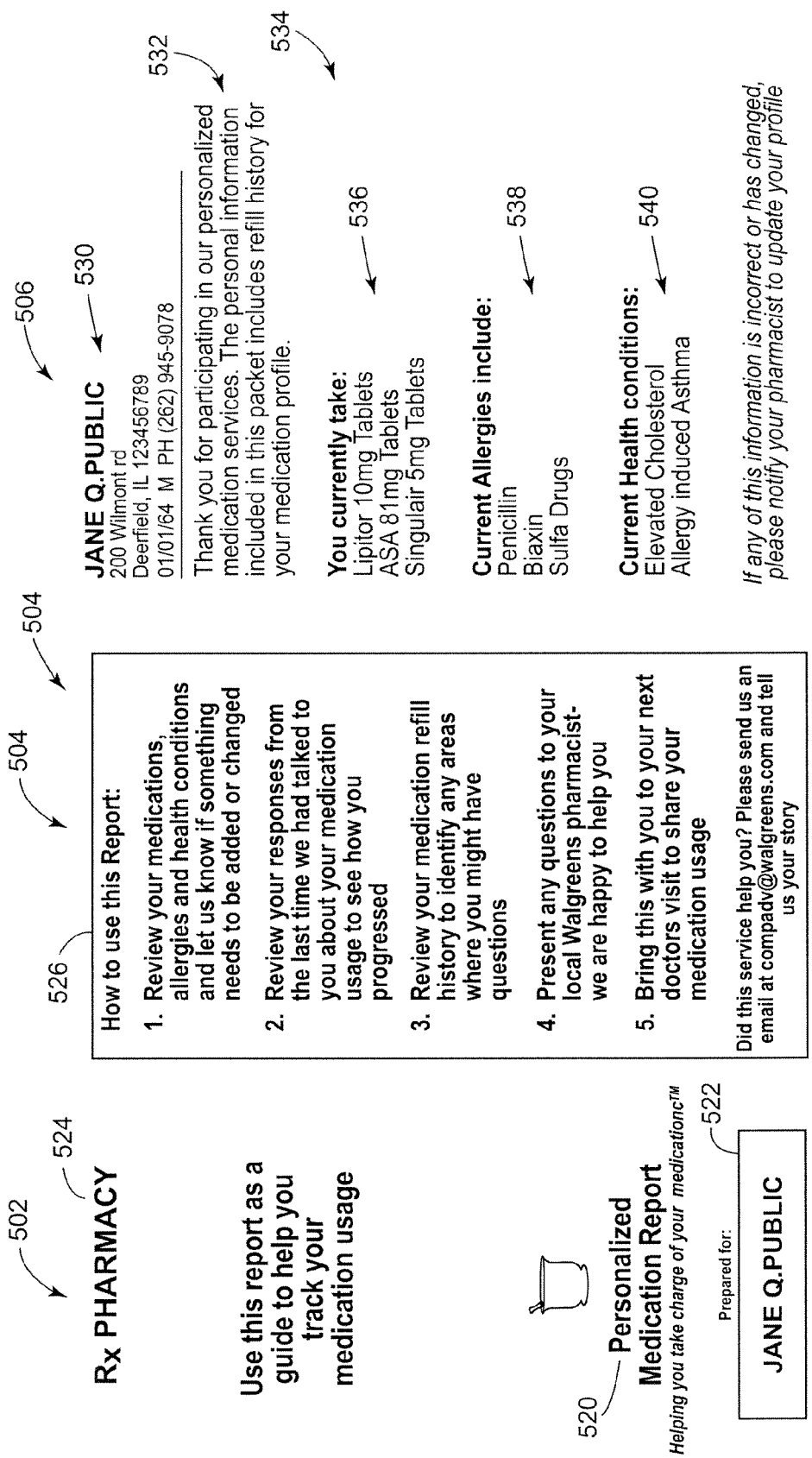
FIG. 11 is a is a sample patient compliance report card.
Figure 11B:
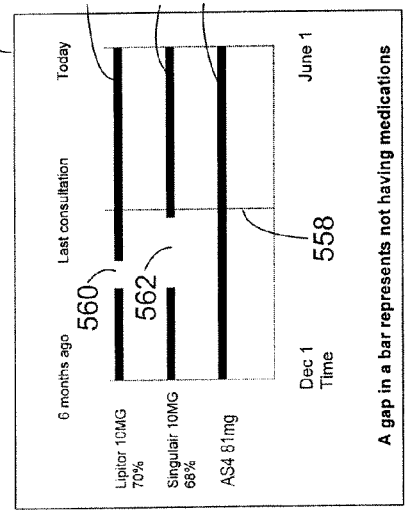

FIG. 11 shows a sample compliance report card 500. A cover page 502 identifies the report card and identifies the patient 516 for whom it is prepared. The cover page 500 may also identify the pharmacy 524 that prepared the report card. The second page 504 of the compliance report card 500 includes a set of instructions 526 for using the report card. The third page of the report card 506 includes the patient's personal information 530 including the patient's name, address, date of birth, sex and home phone number. A brief introductory paragraph 532 is followed by a summary of the patient's medical profile 534. The medical profile includes the patient's current medications 536; current allergies 538; and current health conditions 540. In the example shown, Jane Q. Public of 200 Wilmot Road, Deerfield, Ill. 12345, born Jan. 1, 1964, female, having the phone number (262) 867-5309 is actively taking Lipitor 10 mg tablets, ASA 81 mg tablets and Singulair 5 mg tablets. Ms. Public is allergic to Penicillin, Biaxin and Sulfa drugs. She currently suffers from elevated cholesterol and allergy induced asthma.

Medication possession ratio (MPR) is a measure of a patient's compliance with his or her medication therapy. A patient's medication possession ratio is defined as the number of days supply of medication that the patient has in his or her possession over a specified number of days divided by the specified number of days. The fourth page of the report card 508 includes a chart 550 illustrating the patient's medication possession over the period of time covered by the report card. The patient Jane Q. Public had a service intervention comprising a consultation with a pharmacist on March 1, 558. The chart 550 extends from Dec. 1, three months before the service intervention 558, to Jun. 1, three months after the service intervention 558. The chart 550 shows the patient's medication possession 552, 554, 556 for each of her maintenance medications. As can be seen, a narrow gap 560 appears in her Lipitor possession graph 552 and a somewhat wider gap 562 appears in her Singulair possession graph 554. No gaps appear in her ASA possession graph 556. The gaps 560, 562 indicate periods during which the patient was not in possession of her maintenance medications. Overall, the patient's MPR was 70% for Lipitor and 68% for Singulair. The patient was in possession of her ASA medication at all times, resulting in a 100% MPR for her ASA prescription. Both of the gaps 552, 554 in the patient's possession of Lipitor and Singulair appear in the period of time before the service intervention 558. It appears, based on a review of the patient's MPR, that the patient's compliance improved after the service consultation 558.

The next page of the patient's compliance report card 500 is a questionnaire summary and update page 510. The questionnaire summary and update page 510 includes questions from the initial consultation questionnaire that the patient completed during her initial consultation with the pharmacist. The questions included on the questionnaire summary and update page 510 are selected based on the patient's answers during the initial consultation. Only the questions that were the most significant in terms of identifying the patient's compliance barriers are included in the compliance report card. The original questions 580, 582, 584 are restated, along with the patient's previous responses 586, 588, 590. The patient is then asked how they would answer now? what has changed since the last consultation? what has made compliance better? what has made things worse? for each of the selected questions 580, 582, 584.

The next page 512 of the patient's compliance report card 500 includes a list of possible goals 600 the patient may work towards before the next consultation with the pharmacist. The list of goals 600 may include a number of pre-selected goals or the pharmacist may simply check off those goals that he or she believes would be most beneficial for the patient to work to achieve in the weeks ahead.

Next, a health tips page 514 may include general health tips 610 or other ideas for the patient to keep in mind while managing her medications. This page may also include a section 612 for the patient to write notes or jot down questions that she may have for the pharmacist at their next meeting.

A final page 516 of the compliance report card 500 may provide a list 614 of the compliance related services offered by the pharmacy. This may provide the patient another opportunity to review the compliance services offered by the pharmacy and select additional services if desired. The list of services 614 on the compliance report card 500 may be substantially identical to the list of services included in the medication management Solutions Guide 400 given to the patient at the end of her initial consultation with the pharmacist.

If a patient selects the medication manager service, the medication management system prepares a customized medication management chart for helping the patient keep track of his or her medications. The medication management chart may be given to the patient when he or she picks up her medications, or in conjunction with a consultation with the pharmacist. Alternatively, medication management charts may be mailed to the patient, e-mailed, posted to a secure web cite, or otherwise delivered to the patient. A sample medication management chart 700 is show in FIG. 12. The medication management chart 700 includes the patient's name and personal information 702. The chart is organized as a series of rows 704, 706 708, etc. Each of the patient's medications is listed on a separate row. In the example shown the patient is taking three different medications. Aciphex 20 mg tablets are listed in the first row 704. Glipizide 10 mg tablets are listed in the second row 706. An Intal Inhaler is listed on the third row 708. The blank rows 712, 814 may be used by the patient to record the use of other medications, such as over the counter drugs, vitamins, aspirin, and the like, or to record daily measurements such as blood pressure, glucose levels, and so forth. Each row that lists a medication 704, 706, 708 includes the name of the drug 716, the form in which the drug is provided 718, and a brief description of the medication's appearance or how it is packaged 720. The instructions 722 for taking each medication are also included on each corresponding row.

Horizontally the chart 700 is divided into seven columns representing the seven days of the week. The headings of the columns 730, 732, 234, 736, 738, 740, 742 may be left blank so that the patient may begin the program on any day of the week that he or she sees fit. When the patient begins the program he or she can pencil in the days of the week beginning with the day on which he or she starts the program. Each column includes a number of check boxes 750 in each row. The check boxes in each column correspond to the individual doses of the medication listed on the corresponding row that the patient must take that day. Thus, if a particular medication is to be taken four times per day, four check boxes will appear in each column of the row listing the particular medication.

It is assumed that the patient will take each corresponding dose at or about the same time on each subsequent day. The first column 730 includes blank spaces 752 next to each check box 750 to allow the patient to write in the times he or she takes each dose, in order to customize his or her medication routine according to his or her own schedule. The patient may place a check mark in each box when he or she takes the corresponding dose each day. In this way, the patient may keep track of each dose of his or her medication to ensure that doses are not missed or that doses are accidentally taken twice. The chart 730 may further include spaces for the patient to write down notes for his or her doctor 760, for the pharmacist 762, and to list any side effects he or she is experiencing, or any other comments 764.

If a patient selects a personalized medication record (PMR) service the medication management system may periodically prepare a personalized medication report. A PMR is a document that includes important information about the patient, the patient's health, and the patient's medication history. The patient may carry the PMR with them in case of emergency. Emergency personnel may refer to the PMR to learn about the patient's health status and so forth. The patient may show the PMR to his or her doctor to provide an overview of his or her health status, medication record, and so forth. A new PMR may be prepared for the patient each time the patient has a new prescription filled, or each time a prescription changes, and so forth. The patient may be provided with a protective sleeve or cover so that the patient may insert a copy of his or her PMR into the sleeve or cover each time the patient receives and updated version.

Figure 13:
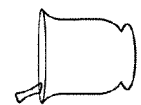
FIG. 13 is a sample personal medication record (PMR).

FIG. 13. shows a sample PMR 800. A cover page 802 identifies the document as a personalized medication record 804 and identifies the patient 806 for whom it is prepared. The cover page 802 may also identify the pharmacy 808 that prepared the PMR. The second page 810 includes a set of instructions 812 on how to use the PMR 800. The next page 814 lists the patient's name and personal information 816. This page may also include various medical and emergency information. For example the page 814 may include the patient's doctor's name and contact information 818, the patient's pharmacy information 820, emergency contact information 822, current allergies 824, and current health conditions 826. A next page 830 may include a list of current medications 832. Finally, a last page 840 may include a list of services 842 offered by the pharmacy with checkmarks indicating which services the patient currently receives.

Patients taking one or more maintenance medications for an extended period of time are the patients who would benefit most from a medication management program. A pharmacy implementing a medication management system may rely on advertising and other efforts to get the word out to patients about the medication management services offered by the pharmacy. However, this requires patients to self identify themselves as candidates for medication management services, and requires patients to take the first step in seeking out such services. A more proactive approach is for the pharmacy to identify those of its patients who would benefit from a medication management program and take the active steps of contacting those patients and offering them medication management services. Therefore, an embodiment of a medication management system includes a point of sale (POS) blocking feature. According to this embodiment patients who may benefit from medication management services are identified and are blocked at the point of sale when having their prescriptions filled. Blocking the transaction allows a pharmacist to explain the pharmacy's medication management program to the patient and determine whether the patient may want to participate.

Returning again to FIG. 3, the pharmacy front end systems 102 include one or more pharmacy workstations 132 and one or more POS terminals 138 located at retail branch stores 144. The POS terminal 138 performs typical cash register functions and accounting functions related to the sale of prescription drugs. Both the pharmacy workstations 132 and the POS terminals 138 are connected to the in-store data network 134. The in-store network 134 may be connected to an in-store application server 134 which connects to the pharmacy back-end systems 104 via an external network 130 as has already been described. The POS terminal 138 includes a small LCD screen or other type of display 140 for displaying messages to the pharmacist operating the POS terminal 138. The POS terminal 138 further includes a bar code reader 140 for reading the bar codes on product packaging, including the bar codes on the packaging of prescription drugs prepared by the pharmacist to fill patient prescriptions.

When a patient comes to the pharmacy to have a prescription filled, the pharmacist pulls up the patient's profile on the workstation 132 as has been described. The pharmacist enters the prescription using the pharmacy legacy systems 150 and prepares the medications to fill the prescription. When the pharmacist enters the prescription, the patient profile is analyzed by the intervention engine 120 executed by the central processing systems 106. The intervention engine 120 includes a number of rules for identifying patients who should be stopped at the point of sale when they attempt to pay for their medications. For example, a rule may be established to block all patients taking maintenance medications who are not participating in a medication management program. When the pharmacist enters the patient's prescription the intervention engine 120 analyzes the patient's profile, including the patient's prescription fill history, to determine whether the patient is taking maintenance medications and if so whether or not the patient is already participating in a medication management program. If the patient meets the conditions of the rule, the intervention engine 120 may issue a POS block by setting a flag in the patient's profile. The flag set in the patient profile indicates that the patient's transaction is to be blocked when the patient returns to pick up and pay for his or her medication.

Back at the pharmacy, the pharmacist prepares the patient's medication. The medication packaging includes a bar code identifying the prescription to which the medication relates. When the patient returns to pick up the medication the pharmacist scans the bar code on the medication packaging using the bar code reader 142. The POS terminal 138 uses the information from the bar code to access the prescription data entered by the pharmacist and stored in the legacy system data stores 152, and the corresponding patient profile. The patient profile includes the POS block flag that was set by the rules engine 118 when the prescription was entered by the pharmacist. The POS terminal 138 is barred from completing the transaction while the POS block flag is set. A message is displayed on the POS terminal's LCD display 140 indicating that the transaction has been blocked. The pharmacist returns to the pharmacy workstation 132 to learn the reason why the transaction was blocked. The pharmacist accesses the patient's profile and a message is displayed indicating that the transaction was blocked because the patient is a candidate for participating in a medication management program. The pharmacist may then consult with the patient, explaining the medication management program to the patient, and asking whether the patient would like to participate in the program. If so, the pharmacist enrolls the patient in the medication management program as has already been described. If not, the pharmacist records that a consultation has taken place but that patient declined to enroll in the medication management program. In either case, the desired message has been delivered to the patient and the POS block flag may be cleared in the patient's profile, and the patient's transaction for the purchase of his or her medications may proceed unhindered. If the patient declines to participate in the medication management program he or she may be blocked again on subsequent visits to the pharmacy unless and until the patient decides to enroll in the medication management program.

According to an embodiment of a medication management system, the POS blocking feature may be expanded to block patients at the point of sale for reasons other than making them aware of the pharmacy's medication management program. According to this embodiment patients sharing one or more common characteristics may be blocked at the point of sale until some specified action is taken. For example, campaigns may be implemented for contacting certain classes of patients in order to deliver messages directed toward the members of the various classes. Campaigns may provide customized interactions with the pharmacy's patients on behalf of the pharmacy itself or on behalf of third-party stakeholders.

Once enrolled in a campaign, a patient may be blocked during future visits to the pharmacy in order to deliver additional messages related to the campaign or to ensure that additional actions related to the campaign are carried out.

The pharmacy may implement campaigns as a paid service to third-party stakeholders. Stakeholders may be willing to pay the pharmacy for delivering messages to various groups of patients, gathering information from such patients or performing some other customized interaction with such patients. A customized interaction may include, for example, asking patients a series of questions related to their medication therapy and recording their responses. The medication management system data may provide the captured data to the third party who requested the campaign on a reimbursable basis. The captured data may be returned to the stakeholder in substantially any format desired. For example, the medication management system may generate customized reports on a periodic basis incorporating the cumulative responses of many patients, or the medication management system may forward patient responses to the third party stakeholder as soon as they are recorded. The reporting mechanism may be established on a case by case basis with the third party stakeholder who is requesting the campaign. The third party may be charged a flat fee for implementing a campaign, or may be charged individually for each patient interaction, or some other billing structure may be implemented.

According to an embodiment of a medication management system, a web-based campaign management tool is provided for creating and managing campaigns for identifying patients and taking actions directed toward identified patients. According to this embodiment campaigns include attributes and components. Table 1 describes the various campaign attributes according to an embodiment of a campaign management tool. Table 1 includes the attribute name, a description of the attribute and valid values that the attribute may take on.

TABLE 1

Campaign Attributes

| Attribute | Description | Valid Values |
|---|---|---|
| 1) Campaign ID | Unique; System Generated; Generated for every new campaign This is created upon saving the campaign. | This should always be unique |
| 2) Campaign Name | Name of the campaign A campaign created from copy create will have as default file name "Copy of <Campaign Name>" but this can be edited The campaign name will include some attribute values | No data validation |
| 3) Campaign Description | A brief description on what the campaign is about, target audience This should be a maximum of 500 characters | No data validation |
| 4) Campaign Start Date | Can only be changed if the campaign has not been activated. Once active it can't be changed | When creating or activating a campaign it should be at least equal to the current date + 1 day and not later than the end date. Illustration: Creation Date is 1 Feb 2007 Start Date should be equal or greater than 2 Feb 2007 |
| 5) Campaign End Date | Can only be changed if the campaign has not been activated. Once active it can't be changed | When creating or activating a campaign it should not be earlier than the start date. |
| 6) Campaign Priority | The priority will decide which campaign will be "offered" to the patient. This is reference point in case patient was hit by multiple campaigns | This can be numeric, descriptive (e.g., high, low), or whatever (yet to be defined) |

TABLE 1-continued

Campaign Attributes

| Attribute | Description | Valid Values |
|---|---|---|
| 7) Campaign Coordinator | This could be the name, department, an organization | No data validation |
| 8) Campaign Coordinator Contact Details | This could be the phone number, email address just in case there would be some concerns on the campaign | No data validation |
| 9) Cost | | Mandatory field<br>This should be in dollar |
| 10) Expected Result | | Mandatory text field<br>No data validation |
| 11) Campaign Status | | Inactive, active, terminated, suspended, completed |
| 12) Sponsor | Name of group, organization sponsoring the campaign | Optional text field<br>No validation |
| 13) Payor | Name of the company, organization funding the campaign | Optional text field<br>No validation |
| 14) Fee Structure | | Optional text field<br>No validation |
| 15) Fee | | Optional text field<br>No validation |
| 16) Billing | | Optional text field<br>No validation |
| 17) Collect Billing Information | | Optional text field<br>No validation |
| 18) Impact | This is just a text box.<br>This is the probable number of patients that may be hit by the campaign | Optional text field.<br>No validation |
| 19) Implementation Procedure | This can be a 1,000-character text description of how the campaign will be implemented | Optional text field<br>No validation |

Table 2 describes the various components of a campaign according to an embodiment of a campaign management tool. Table 2 includes the component name and a brief description of the component.

TABLE 2

Campaign Components

| Component Name | Description |
|---|---|
| 1) Questions | Asking the patient a set of questions. The answer to the questions may or may not lead to service recommendation<br>Not all campaigns will have this component<br>The answers to the questions may not be limited to a range of ratings (1 to 7), but it can be "Yes" or "No," and other that's not numeric. |
| 2) Services | The service may not necessarily be triggered by the questions.<br>Illustration:<br>Generate a report card for the patients on ABC medications.<br>Not all campaigns will have this component.<br>The service can be selected from the existing services defined in a Service table. |
| 3) Rules for Identification | These are the rules that identify the type of patients for the campaign. A patient can be identified by anything on his profile including the campaign he/she participated in.<br>This is a mandatory campaign component. |
| 4) Reporting | Provides the ability to generate statistics related to the campaign |
| 5) List Generation | This could be materials to educate the patient sent via mail. This could also be a list to call.<br>Not all campaigns will have this component. |
| 6) POS Block | The patient is blocked at the store upon dropping a script.<br>Not all campaigns will have this component. |
| 7) Termination | This is a constant component for all campaigns.<br>This defines the process of terminating a campaign. |

TABLE 2-continued

Campaign Components

| Component Name | Description |
| --- | --- |
| 8) Information Page | Provides a text box where customized messages up to 4000 characters long may be defined. |

Additional components may be defined as needed to meet the requirements of various third party stakeholders who wish to contact patients via the pharmacy's POS Block feature. In fact, a direct user interface feed may be provided to receive text messages or other customized interactions directly from the stakeholders to be included in a campaign.

Finally, components themselves may have attributes. Table 3 describes the various attributes that campaign components may include.

TABLE 3

Attributes of the Components

| Attribute | Description |
| --- | --- |
| 9) Frequency/Schedule | This will define how often the component will happen in a campaign and when (start to end) Example: Send mailer every month to the patient for the next 6 months. Generate the report card every 2 months from the time the patient answered Question Set ABC. If the component is service-related and that service is not yet existing, the service has to be created in the Service Maintenance application first. |
| 10) Campaign Scripting (Messaging) | This is the UI messaging. If it's a POS block scripting, this script will have to go to the campaign landing page in RCA. This attribute can be changed on the condition that the component for which this scripting is for has not started yet (start date is not yet reached). |
| 11) Dependencies | This defines what triggers a component to happen; i.e., answers to the questions, report card printing, etc. |

Once a campaign has been defined it may assume one of many different statuses. Table 4 describes the various statuses a campaign may acquire. Table 4 lists each status, a description of each status and the business rules that follow from a campaign having a corresponding status.

TABLE 4

Campaign Status

| Status | Definition | Business Rules on the Status |
| --- | --- | --- |
| Inactive | The campaign has not been activated | Default campaign status Modifications allowed This can be deleted |
| Active | The campaign has been activated even if the start date is still on a later time. | Modifications not allowed after activation If the campaign is activated on a later date than the start date, require new start date. Cannot be deleted Can be suspended, terminated, completed |
| Suspended | The campaign is temporarily stopped with the intention of resuming | Modifications not allowed If the end date was reached and campaign is still suspended the campaign will automatically be terminated Cannot be deleted Can be reactivated. Once reactivated it will be active again |

TABLE 4-continued

Campaign Status

| Status | Definition | Business Rules on the Status |
| --- | --- | --- |
| Terminated | The campaign is permanently stopped before the end date | Modifications now allowed Cannot be deleted Cannot be reactivated |
| Completed | The campaign has reached the end date and the status of the campaign is active or suspended | Modifications not allowed The campaign will take on the completed status a day after the end date Cannot be deleted Cannot be "reactivated" |

Figure 14:
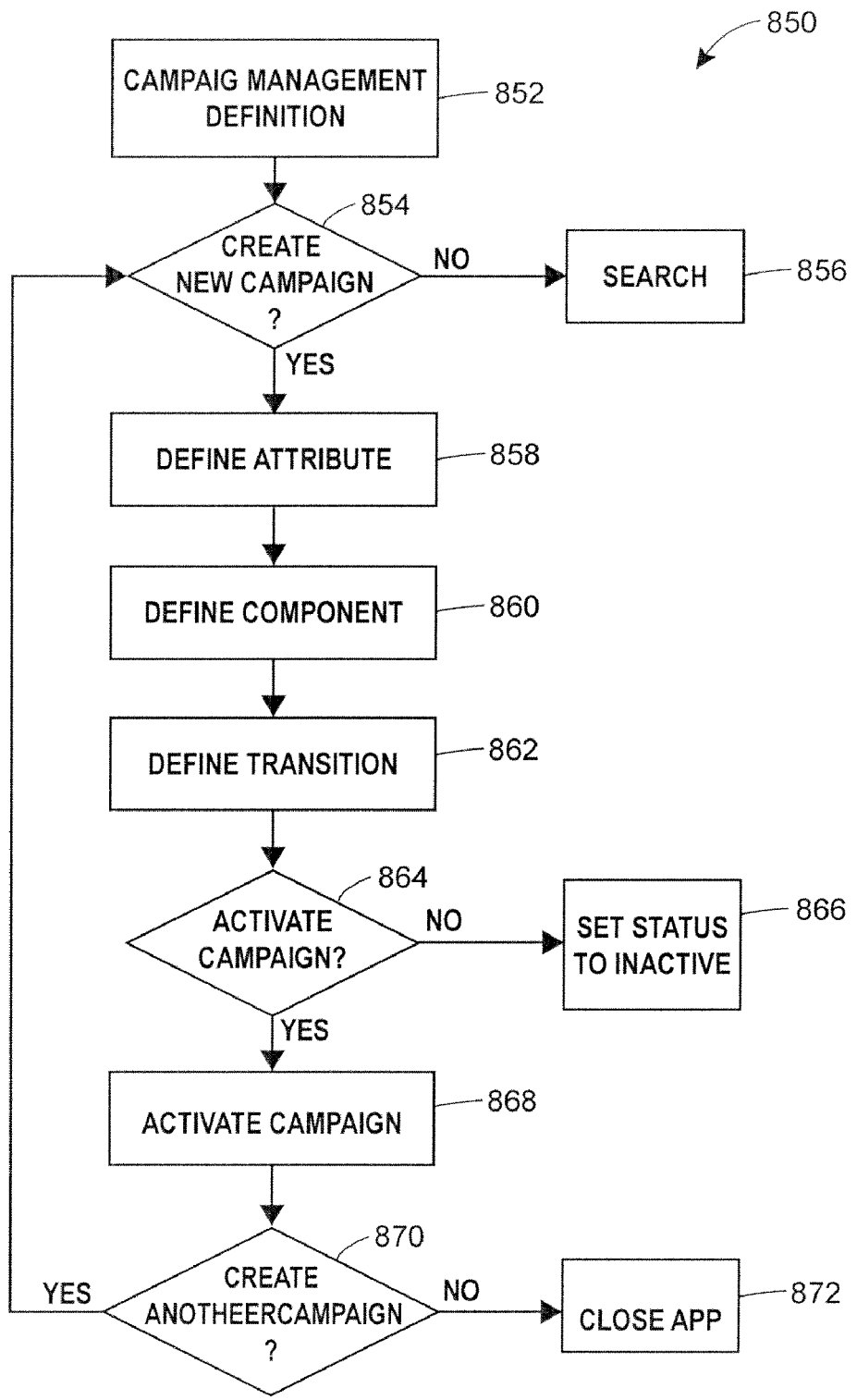
FIG. 14 is a flow chart showing the process flow for defining a targeted campaign for identifying and interacting with patients.

FIG. 14 is a flow chart 850 showing the campaign management definition process flow according to an embodiment of a campaign management tool. The campaign management definition begins at 852. A campaign may be defined from scratch or may be created by modifying an existing campaign. At 854 a determination is made whether the campaign will be a new campaign or based on an existing campaign. If the campaign is to be based on an existing campaign a search for the existing campaign may be performed at 856 and the attributes and components of the existing campaign may be edited to meet the requirements of the new campaign. Otherwise if the campaign is a new campaign, the attributes of the new campaign are defined at 858. The components of the new campaign are defined at 860, and the transitions between the various components are defined at 862. A determination is made at 864 whether or not to activate the campaign. If the campaign is not to be activated the campaign's status is set to inactive at 866. Otherwise, the campaign is activated at 868. A determination is made at 870 whether to create another campaign. If yes, the process returns to 858 where attributes of the next campaign are defined and so forth. If not, the application is closed and the process flow ends at 872.

FIG. 15 shows a campaign attributes interface page 900 for defining or editing the attributes of a campaign. The interface page 900 is part of the campaign management tool, and may be sent to an administrator workstation 140 by the medication management web server 112 (FIG. 3). The interface page 900 includes a number of attribute fields where a user defining a new campaign or editing an existing campaign may enter or change attribute values. Attribute fields are included for entering the campaign name 902; a description of the campaign 904; the campaign priority 906; the name of a campaign coordinator 908; a campaign sponsor 910; a fee structure 912, a billing structure 914; the cost of the campaign 916; the campaign status 918; the campaign start date 920; the campaign end date 922; an expected result 924; the campaign coordinator's contact information 926; the party paying for the campaign 928; the fee 930; and billing 932.

Figure 16:
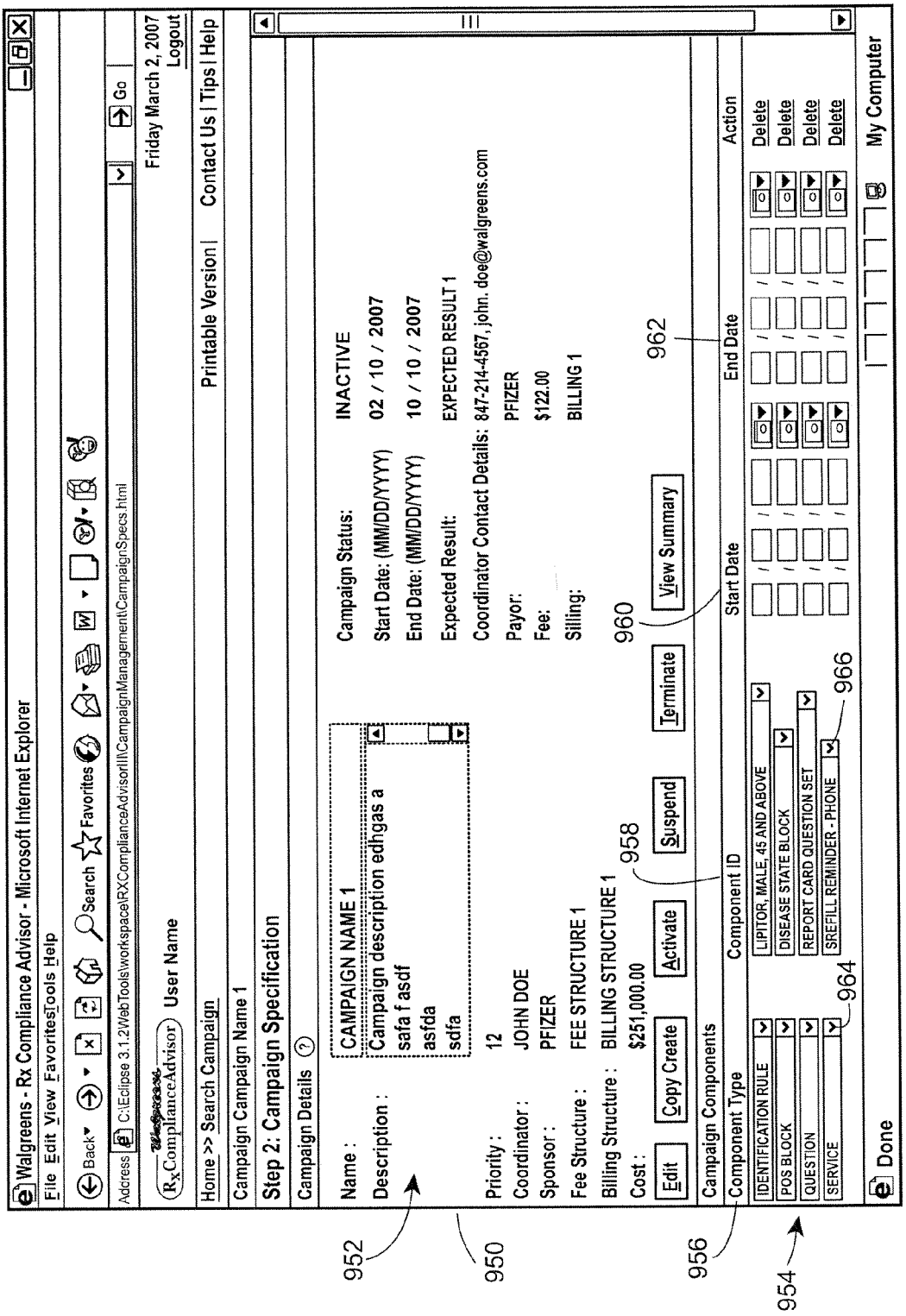
FIG. 16 is a screen shot of a campaign specification user interface page

FIG. 16 shows a campaign components interface page 950 for defining the components of a campaign. The upper portion 952 of the interface page 952 includes a summary of the campaign attributes entered in the attributes interface page 900 of FIG. 15. The bottom portion 954 of the campaign components interface page 950 includes a number of data fields for entering campaign components and related data. A campaign must include at least two components. Generally, these will include a patient identification rule, and some other step. For example, the second step may be delivering a specified message, asking one or more questions of the patient, or some other customized interaction. The campaign components interface page 950 includes data fields for defining the component type 956, the component ID 958, the component start date 960 and the component end date 962. The component type data fields 956 may include drop-down menus 964 from which a user may select the component type for a particular component. The component types listed in the drop-down menu may correspond to the components listed in Table 2. The component ID fields 958 may also include drop-down menus 966 for selecting specific components to be included in the campaign. The component IDs included in the component ID drop-down menu may depend on the type of component selected in the corresponding component type field 956. The campaign start date and campaign end date fields 960, 962 allow the user to enter the dates during which the corresponding component will be active.

Figure 17:
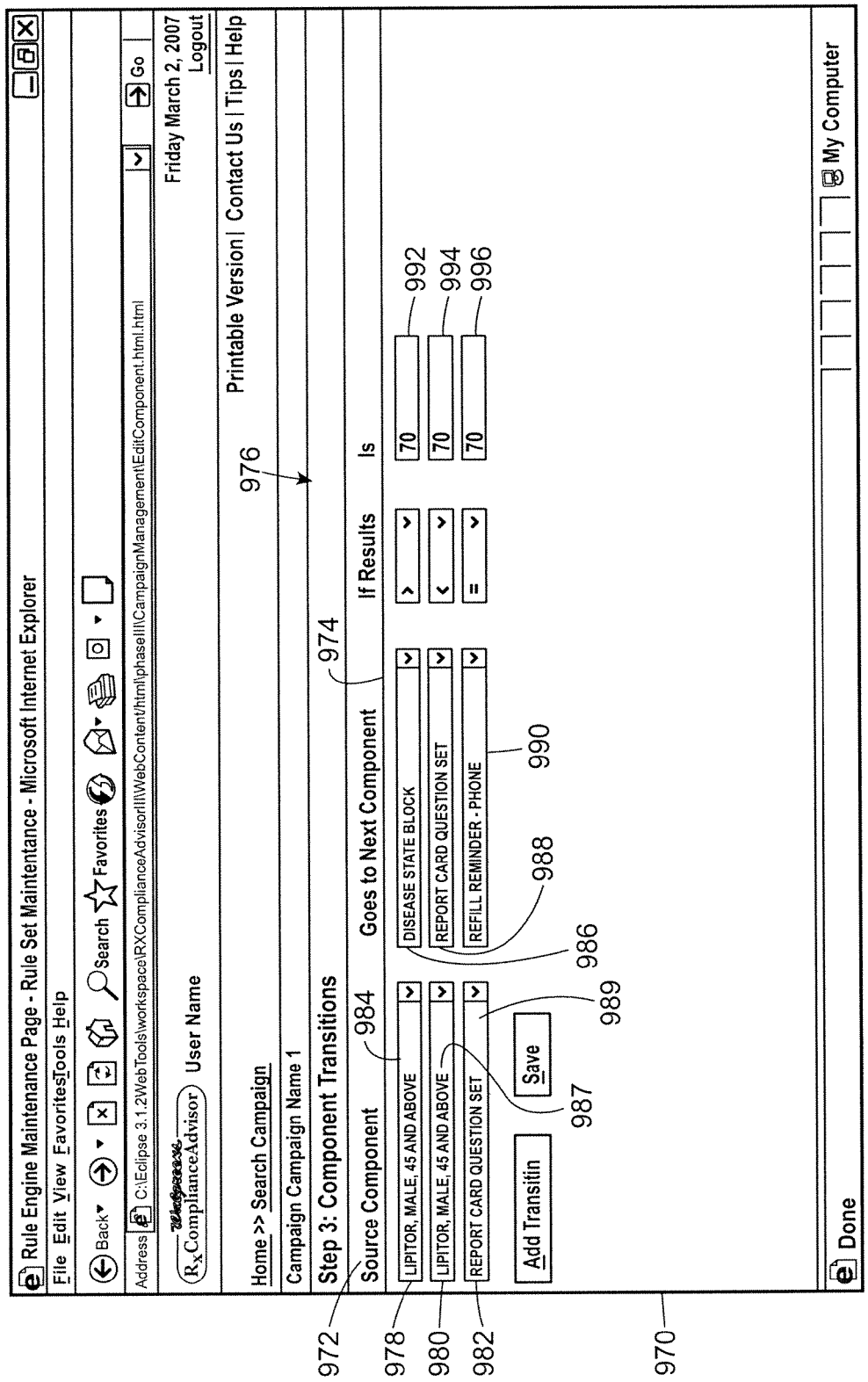
FIG. 17 is a is a screen shot of a campaign component transition definition user interface page.

Finally, FIG. 17 shows a campaign component transition interface page 970. The campaign component transition interface page 970 allows the user to define the transitions between the campaign components selected in the campaign component interface page 950 of FIG. 16. On the campaign component transition interface page 970 the user may select a source component 972 and a destination component 974, and a rule 976 for governing the transition from the source component 972 to the destination component 974. Three conditional transitions 978, 980, 982 are shown in the sample campaign component transition interface page 970. The first two transitions 978, 980, 982 define transitions from the same source component 972, namely, LIPITOR, MALE, 45 AND ABOVE, to different destination components 974 depending on different conditions defined by the corresponding rules 976 defined in each transition 978, 980. In the first transition 978, the campaign will transition from the LIPITOR, MALE, 45 AND ABOVE source component 985 to the disease state block component 986. The transition may be based, for example, on the cumulative score of the patient's responses to a set of questions that form the customized interaction implemented by the campaign. The first transition occurs if the result is greater than seventy 992. In the second transition, from the LIPITOR, MALE, 45 AND ABOVE source component 987 to the report card question set component 988 occurs if the result is less than seventy 994. Finally, in the third transition 982, the campaign will transition from the report card question set source component 989 to the refill reminder-phone component 990 if the result is equal to seventy 996.

Once a campaign has been defined, the campaign management tool interacts with the intervention engine 120 to load the rules for identifying the patients who are the targets of the campaign. Once a campaign has been implemented, the POS block feature works as described above. When a patient contacts the pharmacy to have a prescription filled, the pharmacist accesses the patient's profile and enters the prescription using the pharmacy's legacy systems. The patient's profile is run against the intervention engine 120 to determine whether the patient has the characteristics of the patients targeted by the campaign. If so, an intervention flag is set in the patient's profile. When the patient picks up his or her prescription at the pharmacy, the transaction is blocked at the point of sale by the POS terminal. The POS terminal may display a message indicating that the transaction has been blocked and directing the pharmacist to the pharmacy workstation 132 to learn why the patient was blocked. Upon accessing the patient profile, the pharmacy workstation receives an interface page from the web server 112 that includes a message describing the reason why the patient was blocked as well as the actions that must be taken regarding the patient in furtherance of the campaign. Once the appropriate actions have taken place the intervention flag may be reset in the patients profile, and the transaction allowed to proceed.

As an example, a campaign may be established for providing patients with detailed information about a new medication the first time they have a prescription for the new medication filled. When a patient drops off a prescription for the new medication at the pharmacy the patient's profile is run against the intervention engine 120. The intervention engine may include a rule associated with the campaign for blocking patients the first time they have a prescription for the new medication filled. In this case, if it is the first time the patient is filling a prescription for the new drug, the patient's profile will meet the condition defined by the rule, and the intervention flag will be set in the patient's profile. When the patient picks up his or her prescription, the pharmacist scans the barcode on the prescription packaging, and the POS terminal accesses the patient's profile data. Since the intervention flag is set, the POS terminal will block the transaction and direct the pharmacist to the pharmacy workstation 132. At the pharmacy workstation 132 the pharmacist accesses the patient's profile. An interface page is sent from the medication management web server 112 indicating the reason why the patient was blocked. The pharmacist may then conduct a scripted interaction with the patient based on the particular campaign for which the patient was blocked.

Figure 18:
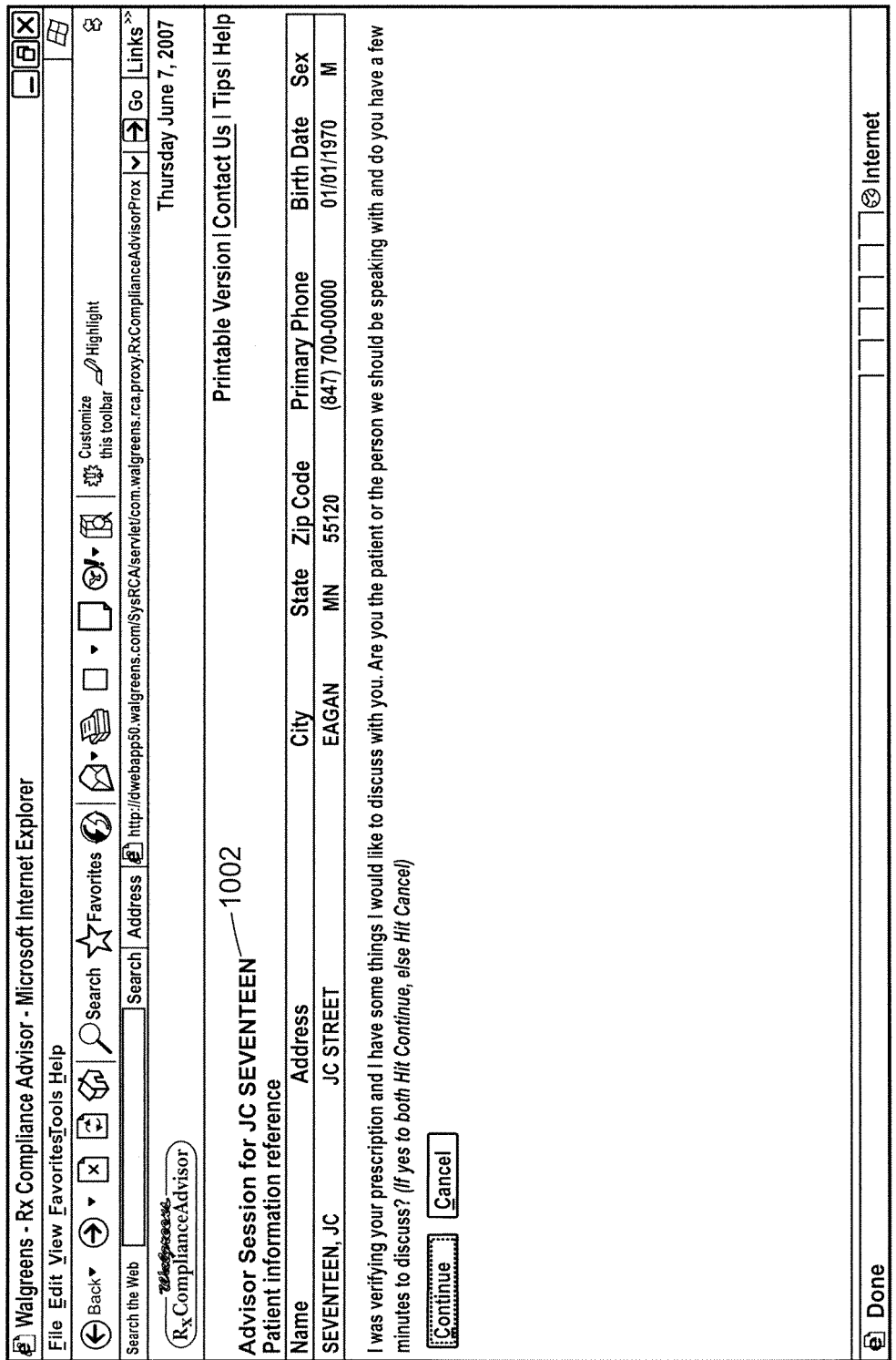
FIG. 18 is a is a screen shot of a campaign information page.
Figure 20:
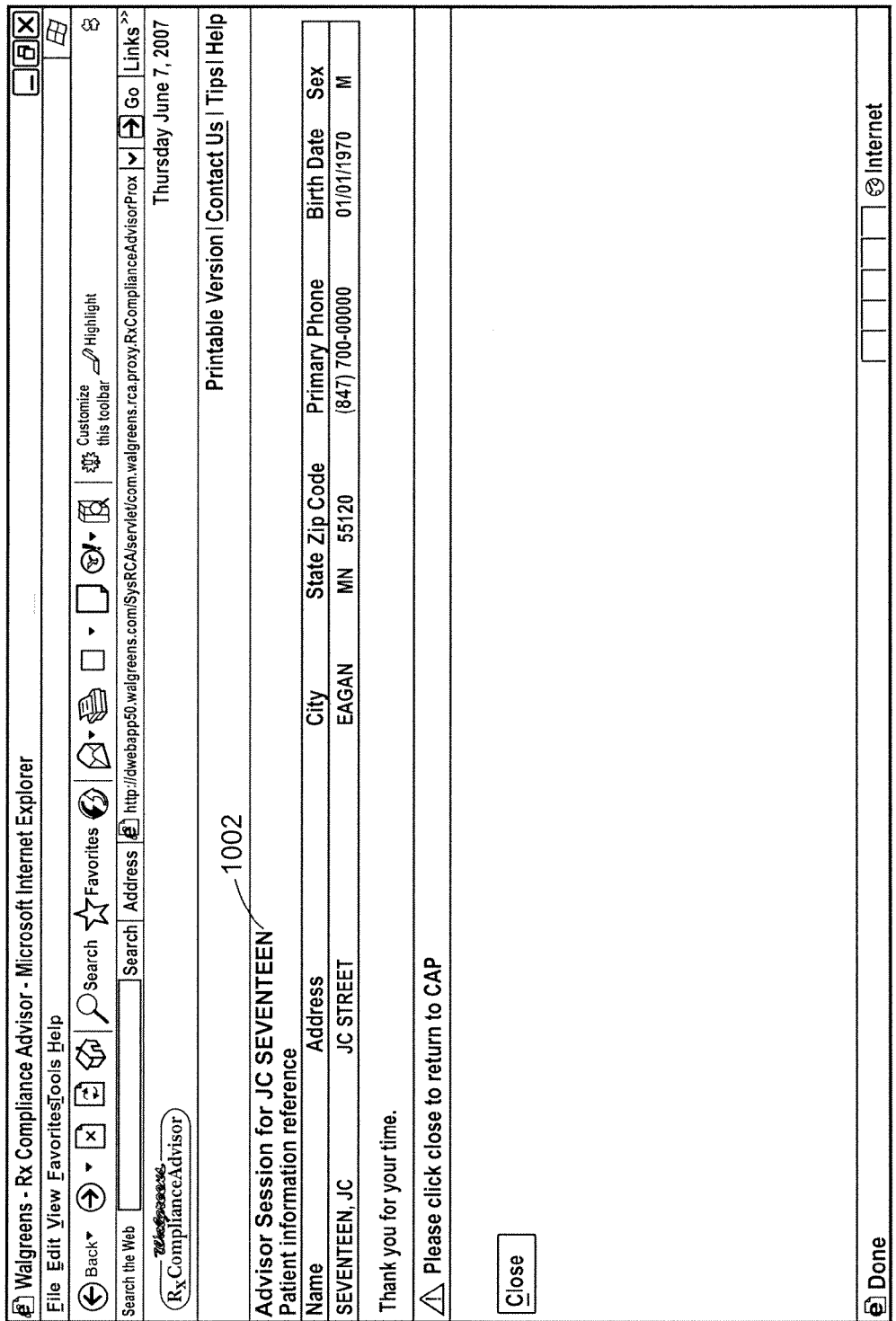
FIG. 20 is a screen shot of a campaign thank you page.

The scripted interaction with the patients may be guided by campaign interface pages sent from the medication management web server 112 to the pharmacy workstation 132. The interface pages associated with a campaign comprise three basic components, an Information page, a Question Set page and a Thank You page. FIGS. 18, 19 and 20 show an Information page 1000, a Question Set page 1020, and a Thank You page 1040, respectively. The Information page 1000 identifies the patient 1002, includes basic patient information 1004 (address, phone number, etc.) and includes a scripted message 1006 for determining whether the patient is in fact a patient having the characteristics of patients targeted by the campaign and whether the patient would be willing to discuss his or her medication therapy. The question set page 1020 includes scripted questions 1022, 1024 associated with the campaign. The pharmacist asks the patient the questions and records the patient's answers by selecting the appropriate radio buttons 1026, 1028, 1030, 1902. In this case, the first question 1022 is merely to confirm that the present prescription fill is the first time the patient has had a prescription for the new medication. The second question is whether the patient would like to receive additional information about the prescribed medication. If the patient answers "yes" to both of these questions, additional information about the medication may be provided to the patient. In either case, once the questions have been asked, and the patient's answers recorded, the required patient level tasks associated with the campaign have been completed with regard to the patient and the intervention flag in the patient's profile may be reset. Once the intervention flag has been reset the POS block is removed and the patient's transaction may be completed. When the pharmacist has entered the patient's answers to the questions the Thank You page 1040 is displayed. The Thank You page may be merely a scripted message 1042 that the pharmacist reads to the patient thanking the patient for participating in the campaign.

Another example of a campaign that may lead to a POS block may relate to periodic tests required of patients taking certain medications. For example, a certain side effect may be associated with a particular drug. Patients taking the drug may be required to take a blood test after a certain period of time to ensure that the negative side effects are not present. A campaign may be established for blocking patients after the defined time period to check whether they have had the required blood test. In this case, a patient taking the medication may be blocked at the point of sale until the patient produces evidence that the requisite blood test has been performed and the results were consistent with continuing to take medication in question.

In yet another embodiment the pharmacy may receive a data feed directly from third party stakeholders identifying patients to be blocked at the point of sale as part of a customized interaction campaign. For example, an insurance company may want to contact all of its patients taking a particular drug to inform them of a cheaper generic equivalent. The insurance company may already know the identity of all the patients in question. The insurance company may feed the list of names to the pharmacy, and a POS block may be established for every name on the list for which the pharmacy has a customer profile. Individual patients on the list may be identified and blocked at the point of sale as has already been discussed, and the appropriate message delivered to the patient at the pharmacy by the pharmacist.

Figure 21:
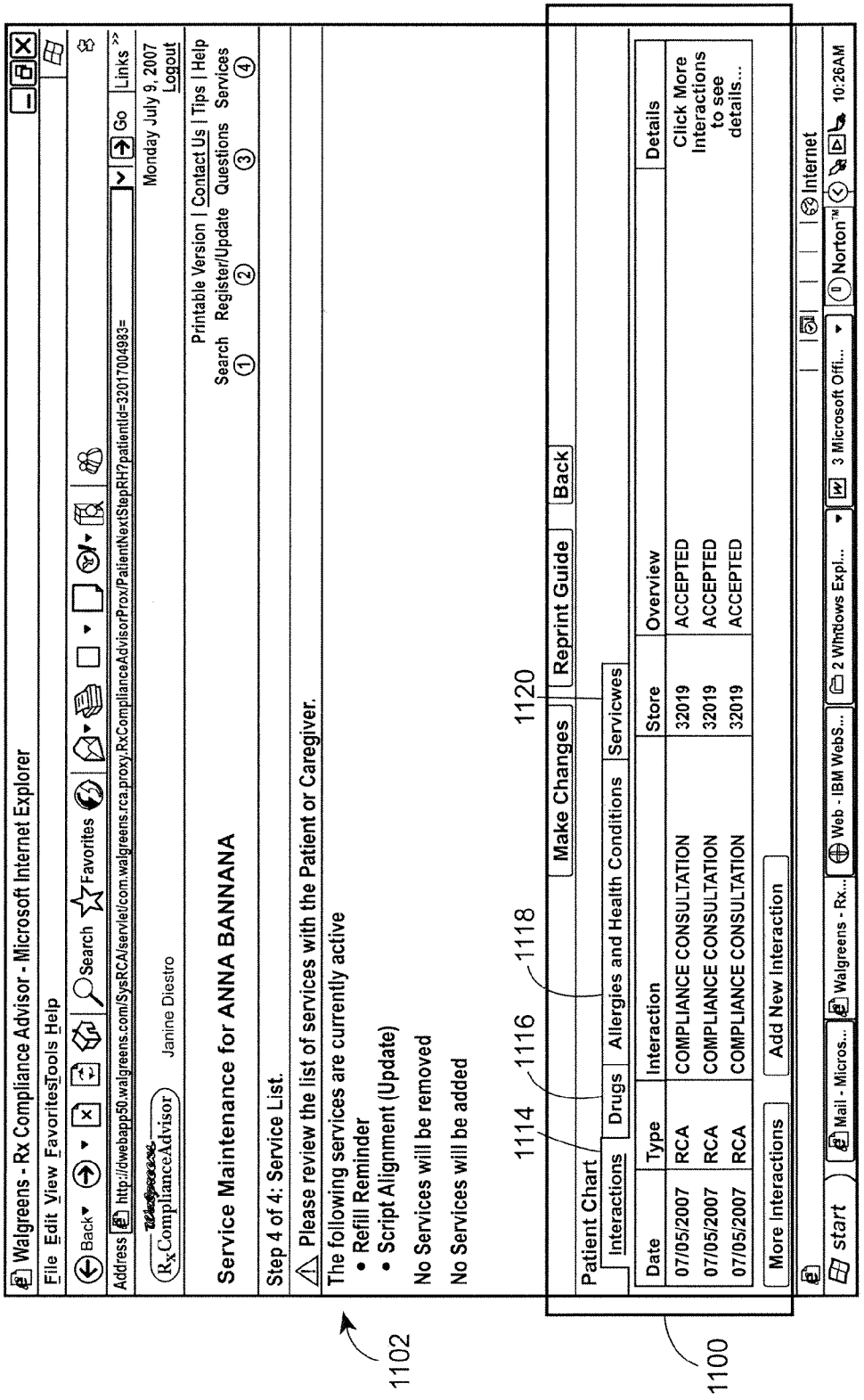
FIG. 21 is a screen shot of a user interface page including a consolidated patient profile view.
Figure 22:
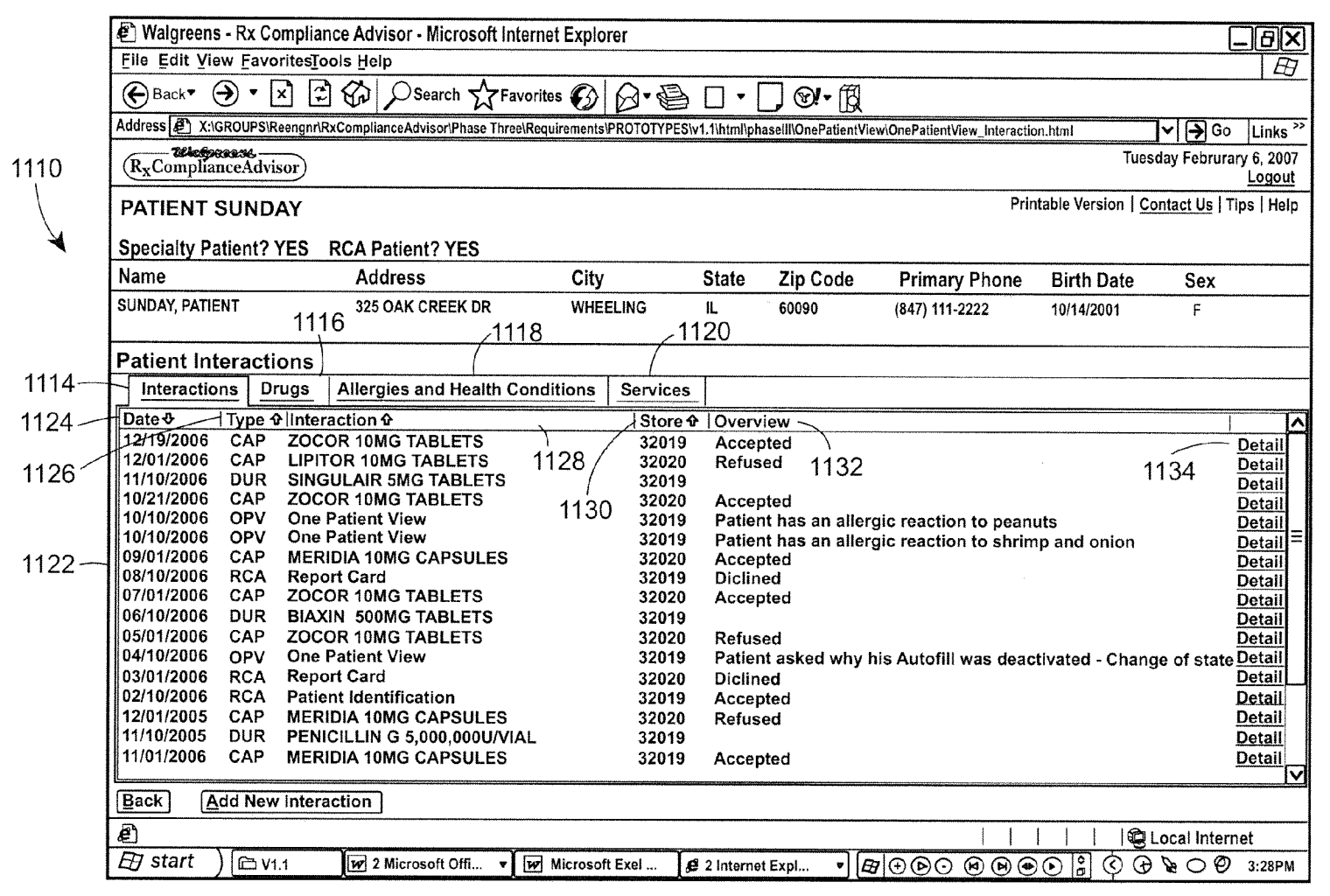

An advantage of a comprehensive medication management system is that a great deal of information about a patient and a patient's medication therapy may be made easily accessible to a pharmacist or other health-care professional. According to an embodiment of a medication management system, a patient's medication data are organized and displayed on an interface in a manner that provides a pharmacist with quick and easy access to all or most of the patient information that the pharmacist needs to perform an informed consultation with a patient. According to this embodiment, the consultation manager 110 may display a consolidated patient profile interface on each page of a web-based consultation interface. FIG. 21, for example, shows a minimized patient chart 1100 displayed along with a service maintenance page 1102. FIG. 22 shows an expanded full-screen view 1110 of the consolidated patient profile. If desired, a pharmacist may expand the minimized patient chart 1100 into the full-screen view 1110 from any consultation interface page (e.g., from a medication management report card consultation page, a script alignment interface page, and the like) provided by the consultation manager 110.

The consolidated patient profile interface, either the minimized version 1100 (FIG. 21) or the full-screen view 1110 (FIG. 22), includes a number of user selectable tabs 1114, 1116, 1118, 1120 for selecting the type of patient data displayed on the consolidated patient profile interface 1100, 1110. The Interactions Tab 1114 causes a list 1122 of all of the interactions that have taken place between the patient and the pharmacy to be displayed. The list 1122 displays the date on which the interaction occurred 1124, the type of interaction 1126, the subject of the interaction 1128, the location (i.e., branch store) at which the interaction occurred 1130 and an overview 1132 of what transpired during the interaction. A detail link 1134 is provided for each interaction. A detail link 1134 links to an interface page that includes additional details about the corresponding interaction.

FIG. 23 shows a full-screen view of a consolidated patient profile 1140 with the Drugs Tab 1116 selected. The Drugs Tab 1116 causes a list 1142 of all of the patient's medications to be displayed. When applicable, the list includes the prescription number 1144 associated with each drug purchase, the name of the drug 1146, the last date 1148 the drug was sold to the patient, and the store 1150 at which the drug was sold.

FIG. 24 shows a full-screen view of a consolidated patient profile 1160 with the Allergies and Health Conditions Tab 1118 selected. The Allergies and Health Conditions Tab 1118 causes a list of the patient's current allergies 1162 and a list of the patient's current health conditions 1164 to be displayed.

Finally, FIG. 25 shows a full-screen view of a consolidated patient profile 1170 with the Services Tab 1120 selected. The Services Tab 1120 causes a list 1172 of the pharmacy services that are currently active in the patient's profile to be displayed. Thus, the web-based consolidated patient profile interface pages shown in FIGS. 21-25 provide the pharmacist with ready access to a wealth of patient information that may be relied on by the pharmacist when the pharmacist is consulting with a patient.

The interface pages displaying the consolidated patient profile may be provided with additional or different display tabs to display additional patient data or patient data that is organized in a different manner, as necessary to provide pharmacists with all of the patient data needed to perform thorough and complete consultations with their patients. Furthermore, patient data from a consolidated patient profile may be made accessible to the patient, the patient's caregiver, the patient's physician or some other authorized party, by posting the consolidated patient profile to a secure website, or otherwise making the data available on a protected basis to the patient and other authorized parties.

Many of the services offered to patients as part of a comprehensive medication management program will require individual pharmacists to perform certain tasks. For example, an auto-refill service will require a pharmacist to prepare the prescriptions that are automatically being refilled. Preferably the prescriptions will be prepared by a pharmacist at the local branch store where the patient typically has his or her prescriptions filled. Similarly, for patients who have signed up to receive personal calls when their prescription refills are due, or past due, or when their prescriptions are ready, a pharmacist must be tasked with placing the call. Again, it is preferable that the pharmacist who places the call is a pharmacist at a branch store where the patient typically has his or her prescriptions filled.

According to an embodiment of a medication management system 100 (see FIG. 3) the task list generator 124 periodically performs batch processes to identify patients who are receiving services that require some action to be taken over a specified period of time. The task list generator identifies the tasks that must be performed (e.g., re-filling specific prescriptions, placing re-fill reminder telephone calls, and so forth) and identifies the various branch stores or other locations where it is most appropriate for the various tasks to be performed. The task list generator then prepares lists of tasks to be performed at the various branch stores or other locations. Individualized task list interface pages may be sent from the medication management web server 112 to the pharmacy workstations 132 at the various branch stores and other locations where the tasks are to be performed. The pharmacists at the various branch stores and other locations may review the individualized task list for his or her location, and perform the various tasks described on the individualized task list interface page as part of his or her daily responsibilities.

Figure 26:
FIG. 26 is a screen shot of a pharmacist task list interface page.

FIG. 26 shows an example of a pharmacist task list interface page 1200. The task list interface page 1200 may be divided between a pharmacist schedule 1202 and a pharmacist task list 1204. On the pharmacist schedule 1202 portion of the pharmacist task list interface page 1200 individual tasks 1206, 1208 are scheduled for specific times of the day they are to be performed. Thus, the pharmacist reviewing the pharmacist task list interface page 1200 will know that at 10:00 on May 1$^{st}$, he or she must place a refill reminder call 1206 to patient Marie L. Johnson. At 10:30 that day, the pharmacist is scheduled to have a diabetes follow-up consultation 1208 with patient Steven R. Smith. Each scheduled task, 1206, 1208 includes the time 1209 for which the task is scheduled, a description of the task 1210, the name of the patient associated with the task 1212, the patient's primary phone number 1214, and the status of the task.

The lower portion 1204 of the pharmacist task list interface page 1200 merely shows a list of unscheduled tasks that must be performed. The pharmacist may perform each task on an ad hoc basis as time allows throughout the day without regard to a specified time. Each task listed in the list 1204 includes the type of interaction 1218, a description of the task 1220, a task due date 1222, the source or service that generated the task 1224, the priority assigned to the task 1226, and the status of the task 1228. The pharmacist task list interface page 1230 further includes a create new task button 1230 that allows the pharmacist to add new tasks to the list.

By implementing a medication management system as described herein, a pharmacy may better serve its patients by providing services that will help patients improve their compliance with their individual mediation therapies. The pharmacy may also provide valuable services to the broader medical services delivery community by providing access to patients heretofore unavailable to third party stakeholders. Such services may be provided in a setting that will improve the pharmacy's relations with its customers while opening new potentially lucrative revenue streams based on providing reimbursable cognitive services to the third party stakeholders.

While the preceding paragraphs describe several exemplary embodiments of a prescription alignment system, the various embodiments described are not intended to limit the invention to the individual embodiments. Various aspects of the alternate embodiments may be combined in varying ways to create the system and method that best suits the pharmacy implementing the system and method, the pharmacy's customers, and the regulatory environment in which the pharmacy operates

The invention claimed is:

1. A method for improving an individual patient's compliance with a prescribed medication therapy, the method comprising:
    creating a medication management program including a plurality of services for improving patient compliance, each service designed to address one or more compliance barriers and the plurality of services including at least one of: automatic prescription refills for maintenance medications; patient-pharmacist consultation services; customized dose charts; express payment services; pill box services; pill box counseling; multi-dose packaging; multi-dose-services; multi-dose counseling; compliance packaging; refill reminder services; discount medication programs; frequent prescriber programs; script alignment services; or health/medication information services;

executing an intervention engine when a prescription associated with the individual patient is entered, the intervention engine determining if the individual patient is a candidate for participating in the medication management program based on rules for identifying the individual patient for the medication management program;

based on a determination made by the intervention engine that the individual patient is a candidate for participating in the medication management program, displaying a message when the individual patient picks up the medication related to the prescription that the individual patient is a candidate for participating in the medication management program;

based on a determination made by the intervention engine that the individual patient is a candidate for participating in the medication management program, storing data about the individual patient on non-transitory computer readable medium, the data corresponding to individual patient's responses to a series of questions presented to the patient by a pharmacy employee;

executing a rules engine on a computer processor for analyzing the patient data stored on the computer readable medium to identify one or more compliance barriers facing the individual patient and selecting at least one service designed to address at least one of the one or more identified compliance barriers from the plurality of services, wherein the analyzing comprises evaluating the individual patient's responses and the selecting comprises selecting a service based on a significance associated with one or more of the individual patient's responses;

wherein the executing a rules engine comprises mapping questions to the services, and selecting a service according to a clinical significance of at least a portion of the individual patient's responses to the questions mapped to the services;

offering the at least one selected service to the individual patient; and activating the at least one selected service only if an agreement response is received from the individual patient.

2. The method of claim 1 further comprising providing a response scale associated with each question whereby the individual patient may respond to the questions with a quantified response within the response scale that is related to the significance associated with the one or more of the individual patient's responses by the individual patient.

3. The method of claim 2 wherein the response scale comprises a seven-point readiness ruler in which a response of 1 signifies a negligible compliance barrier and a response of 7 signifies a significant compliance barrier and responses between 1 and 7 signify a proportional compliance barrier along the scale from 1 to 7.

4. A system for identifying a compliance-related service from a medication management program, the system comprising:

a workstation implementing a web browser, the workstation disposed in a pharmacy;

a web server adapted to send web-based interface pages to the workstation over a network, the web-based interface pages adapted to be displayed by the workstation web browser to provide a user interface;

an intervention engine adapted to determine if the individual patient is a candidate for participating in the medication management program, the medication management program comprising a plurality of compliance-related services to be offered to an individual patient, each service designed to address one or more compliance barriers and the plurality of services including at least one of: automatic prescription refills for maintenance medications; patient-pharmacist consultation services; customized dose charts; express payment services; pill box services; pill box counseling; multi-dose packaging; multi-dose-services; multi-dose counseling; compliance packaging; refill reminder services; discount medication programs; frequent prescriber programs; script alignment services; or health/medication information services, based on rules for identifying the individual patient for the medication management program when a prescription associated with the individual patient is entered;

a computerized consultation manager adapted to generate content to be included in the web-based interface pages based on a determination made by the intervention engine that the individual patient is a candidate for participating in the medication management program, including a message displayed when the individual patient picks up the medication related to the prescription that the individual patient is a candidate for participating in the medication management program, a plurality of questions to be presented to the individual patient by a pharmacy employee and one or more selectable responses for storing data corresponding to the individual patient's responses to the questions; and a rules engine adapted to evaluate the individual patient's responses to the questions and selecting appropriate compliance-related services to be offered to the individual patient based on a significance associated with one or more of on the patient's responses, wherein the rules engine is further adapted to map the questions to the services, and to select a service according to a clinical significance of at least a portion of the individual patient's responses to the questions mapped to the services, the consultation manager further adapted to generate controls to be included in the web-based interface pages to selectively activate one or more of the appropriate compliance-related services offered to the individual patient only if an agreement response is received from the individual patient.

5. The system of claim 4 wherein the selectable responses for recording the individual patient's responses to the questions comprise a plurality of discrete values within a response scale that is related to the significance associated with the one or more of the individual patient's responses by the individual patient.

6. The system of claim 5 wherein the response scale comprises a seven-point readiness ruler.

7. The system of claim 5 wherein the rules engine is configured to select one question from among a plurality of questions to which the individual patient answers with like responses on the response scale to take precedence.

8. The system of claim 4 wherein the web-based interface pages comprising the user interface include a user interface page listing the compliance-related services selected by the rules engine.

9. The system of claim 8 wherein the user interface page listing the compliance-related services selected by the rules engine includes provisions for implementing the selected services on behalf of the individual patient.

10. A method of identifying services from a medication management program, the method comprising:

executing an intervention engine when a prescription associated with the individual patient is entered, the intervention engine determining if the individual patient is a candidate for participating in the medication management program, the medication management program including a plurality of services to be offered to a patient for improving the individual patient's compliance with a prescribed medication therapy, each service designed to address one or more compliance barriers and the plurality of services including at least one of: automatic prescription refills for maintenance medications; patient-pharmacist consultation services; customized dose charts; express payment services; pill box services; pill box counseling; multi-dose packaging; multi-dose-services; multi-dose counseling; compliance packaging; refill reminder services; discount medication programs; frequent prescriber programs; script alignment services; or health/medication information services, based on rules for identifying the individual patient for the medication management program;

based on a determination made by the intervention engine that the individual patient is a candidate for participating in the medication management program, executing a consultation manager on a medication management processing system, the consultation manager including a series of questions to be asked of the individual patient;

mapping the questions to various services;

establishing rules for ranking the questions based on the individual patient's responses to the questions;

based on a determination made by the intervention engine that the individual patient is a candidate for participating in the medication management program, displaying a message when the individual patient picks up the medication related to the prescription that the individual patient is a candidate for participating in the medication management program and displaying the questions to be asked of the individual patient on an interface device;

based on a determination made by the intervention engine that the individual patient is a candidate for participating in the medication management program, presenting the individual patient the questions via a pharmacy employee and storing data corresponding to the individual patient's responses to the questions via the interface device;

executing a rules engine on the medication management processing system, the rules engine ranking the questions according to the rules and the individual patient's responses to the questions and identifying one or more services to which one or more highest-ranking questions are mapped and according to a clinical significance of at least a portion of the individual patient's responses to the questions mapped to the services; and displaying controls to selectively activate one or more of the appropriate compliance-related services offered to the individual patient only if an agreement response is received from the individual patient.

11. The method of claim 10 wherein the individual patient's responses are limited to discrete responses selected from a spectrum of possible responses.

12. The method of claim 11 wherein the spectrum of possible responses comprises a seven point readiness ruler that is related to the significance associated with the one or more of the individual patient's responses by the individual patient.

13. The method of claim 11 wherein the rules for ranking the questions based on the individual patient's responses comprise ranking the questions according to the position of each response within the spectrum of possible responses.

14. The method of claim 11 wherein the questions are ranked according to the position of the individual patient's responses to the questions within the spectrum of possible responses and the clinical significance of each question.

15. The method of claim 10 wherein asking the individual patient the questions comprises providing a printed questionnaire to the individual patient.

16. A system for identifying a compliance related service from a medication management program, the system comprising:

an interface adapted to present a message when the individual patient picks up the medication related to the prescription that the individual patient is a candidate for participating in the medication management program and to present a plurality of questions to be asked of the individual patient by a pharmacy employee and storing data corresponding to the individual patient responses thereto; and a computer processor executing:

an intervention engine adapted to determine if the individual patient is a candidate for participating in the medication management program, comprising a plurality of compliance-related services to be offered to an individual patient for improving the individual patient's compliance with a prescribed medication therapy, each service designed to address one or more compliance barriers and the plurality of services including at least one of: automatic prescription refills for maintenance medications; patient-pharmacist consultation services; customized dose charts; express payment services; pill box services; pill box counseling; multi-dose packaging; multi-dose-services; multi-dose counseling; compliance packaging; refill reminder services; discount medication programs; frequent prescriber programs; script alignment services; or health/medication information services, based on rules for identifying the individual patient for the medication management program when a prescription associated with the individual patient is entered; and a rules engine adapted to map individual questions to specific compliance related services, the rules engine further adapted to evaluate the individual patient's responses to the questions presented by a pharmacy employee based on a determination made by the intervention engine that the individual patient is a candidate for participating in the medication management program, rank the questions according to the individual patient's responses, and select a service to which a highest ranking question is mapped and according to a clinical significance of at least a portion of the individual patient's responses to the questions mapped to the services, the interface further adapted to present controls to selectively activate one or more of the appropriate compliance related services offered to the individual patient only if an agreement response is received from the individual patient.

17. The system of claim 16 wherein the interface comprises at least one of a web-enabled workstation adapted to receive interface pages over a network and including a display for displaying the plurality of questions and an input device for entering data corresponding to the individual patient's responses to the questions; or a printed document including the questions and on which the individual patient may record responses to the questions.

18. The system of claim 16 wherein the individual patient's responses are limited to a plurality of discrete values within a range of values defining a response scale that is related to the significance associated with the one or more of the individual patient's responses by the individual patient, and the rules engine ranks each question according to a discrete value assigned to the questions by the individual patient in response to each question.

19. The system of claim 18 wherein the rules engine rank questions in accordance with their clinical significance in cases in which the individual patient assigns the same discrete value from the response scale to more than one question.

* * * * *